United States Patent
Maue et al.

(10) Patent No.: US 9,936,699 B2
(45) Date of Patent: Apr. 10, 2018

(54) HALOGEN-SUBSTITUTED COMPOUNDS

(71) Applicant: BAYER CROPSCIENCE AKTIENGESELLSCHAFT, Monheim am Rhein (DE)

(72) Inventors: Michael Maue, Langenfeld (DE); Tobias Harschneck, Düsseldorf (DE); Julia Johanna Hahn, Düsseldorf (DE); Thomas Bretschneider, Lohmar (DE); Anne Decor, Langenfeld (DE); Reiner Fischer, Monheim (DE); Werner Hallenbach, Monheim (DE); Hans-Georg Schwarz, Dorsten (DE); Robert Velten, Langenfeld (DE); Niels Böhnke, Berlin (DE); Olga Malsam, Rösrath (DE); Ulrich Görgens, Ratingen (DE); Sebastian Horstmann, Leverkusen (DE); Klaus Raming, Leverkusen (DE); Johannes Köbberling, Neuss (DE); Walter Hübsch, Wuppertal (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/501,733

(22) PCT Filed: Aug. 5, 2015

(86) PCT No.: PCT/EP2015/068055
§ 371 (c)(1),
(2) Date: Feb. 3, 2017

(87) PCT Pub. No.: WO2016/020436
PCT Pub. Date: Feb. 11, 2016

(65) Prior Publication Data
US 2017/0223960 A1    Aug. 10, 2017

(30) Foreign Application Priority Data

Aug. 8, 2014 (EP) .................................. 14180334

(51) Int. Cl.
| | | |
|---|---|---|
| *C07D 231/16* | (2006.01) | |
| *C07D 231/18* | (2006.01) | |
| *C07D 231/38* | (2006.01) | |
| *C07D 401/04* | (2006.01) | |
| *C07D 401/14* | (2006.01) | |
| *C07D 403/04* | (2006.01) | |
| *A01N 43/56* | (2006.01) | |

(52) U.S. Cl.
CPC .......... *A01N 43/56* (2013.01); *C07D 231/16* (2013.01); *C07D 231/18* (2013.01); *C07D 231/38* (2013.01); *C07D 401/14* (2013.01); *C07D 403/04* (2013.01)

(58) Field of Classification Search
CPC .. C07D 231/16; C07D 231/18; C07D 231/38; C07D 401/04; C07D 401/14; C07D 403/04
See application file for complete search history.

(56) References Cited

U.S. PATENT DOCUMENTS 9,487,489 B2 * 11/2016 Maue .................... C07D 401/12

FOREIGN PATENT DOCUMENTS

| | | |
|---|---|---|
| EP | 1911751 A1 | 4/2008 |
| WO | 2000/007980 A1 | 2/2000 |
| WO | 2004/035545 A2 | 4/2004 |
| WO | 2004/106324 A1 | 12/2004 |
| WO | 2008/029084 A1 | 3/2008 |
| WO | 2010/051926 A2 | 5/2010 |
| WO | 2012/069366 A1 | 5/2012 |
| WO | 2012/107434 A1 | 8/2012 |
| WO | 2014/122083 A1 | 8/2014 |

OTHER PUBLICATIONS

International Search Report of International Patent Application No. PCT/EP2015/068055 dated Sep. 21, 2015.
Parlow, John J. et al., "Utility of Complementary Molecular Reactivity and Molecular Recognition (CMR/R) Technology and Polymer-Supported Reagents in the Solution-Phase Synthesis of Heterocyclic Carboxamides", Journal of Organic Chemistry, 1997, pp. 5908-5919, vol. 62, No. 17.
Parlow, John J., "Synthesis of Pyrazolecarbonylamino-pyridinecarboxamides as Herbicides" Journal of Heterocyclic Chemistry, 1998, pp. 1493-1499, vol. 35.

* cited by examiner

*Primary Examiner* — Laura L Stockton
(74) *Attorney, Agent, or Firm* — McBee Moore Woodward & Vanik IP, LLC

(57) ABSTRACT

The invention relates inter alia to halogen-substituted compounds of the general formula (I) in which the substituents $A_1$, $R_1$-$R_3$ and $Z_1$-$Z_3$ have the meanings given in the description. Also described are processes for preparing the compounds of the formula (I) and possible intermediates for the preparation of these compounds. The compounds according to the invention are particularly suitable for controlling insects, arachnids and nematodes in agriculture and ectoparasites in veterinary medicine.

18 Claims, No Drawings

HALOGEN-SUBSTITUTED COMPOUNDS

CROSS-REFERENCE TO RELATED APPLICATIONS

This application is a National Stage entry of International Application No. PCT/EP2015/068055, filed Aug. 5, 2015, which claims priority to European Patent Application No. 14180334.6, filed Aug. 8, 2014.

BACKGROUND

Field

The present application relates to novel halogen-substituted compounds, to processes for their preparation and to their use for controlling animal pests, in particular arthropods and especially insects, arachnids and nematodes.

Description of Related Art

It is known that certain halogen-substituted compounds have herbicidal action (cf. J. Org. Chem. 1997, 62(17), 5908-5919, J. Heterocycl. Chem. 1998, 35(6), 1493-1499, WO 2004/035545, WO 2004/106324, US 2006/069132, WO 2008/029084).

Furthermore, it is known that certain halogen-substituted compounds have insecticidal action (EP 1 911 751, WO2012/069366, WO2012/080376 & WO2012/107434).

In addition, it is known that certain halogen-substituted compounds have cytokine-inhibitory activities (WO 2000/07980).

Modern crop protection compositions have to meet many demands, for example in relation to efficacy, persistence and spectrum of their action and possible use. Questions of toxicity, the combinability with other active compounds or formulation auxiliaries play a role, as well as the question of the expense that the synthesis of an active compound requires. Furthermore, resistances may occur. For all these reasons, the search for novel crop protection agents can never be considered as having been concluded, and there is a constant need for novel compounds having properties which, compared to the known compounds, are improved at least in respect of individual aspects.

SUMMARY

It was an object of the present invention to provide compounds which widen the spectrum of the pesticides under various aspects and/or improve their activity.

Surprisingly, it has now been found that certain halogen-substituted compounds and their N-oxides and salts have biological properties and are particularly suitable for controlling animal pests, and can therefore be employed particularly well in the agrochemical field and in the animal health sector.

Similar compounds are already known from WO 2010/051926.

One aspect of the present invention refers to a compounds of the general formula (I),

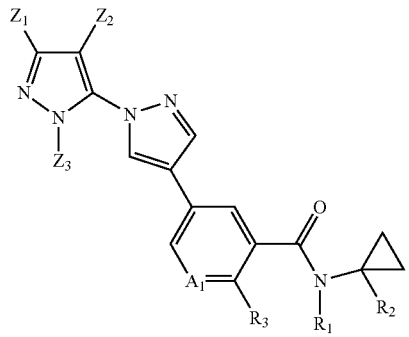

in which
$Z_1$ represents perhalogenated $(C_1$-$C_2)$-alkyl;
$Z_2$ represents —$S(O)_{0-2}$—$(C_1$-$C_2)$-alkyl or —$S(O)_{0-2}$—$(C_1$-$C_2)$-halogenalkyl;
$Z_3$ represents $(C_1$-$C_2)$-alkyl;
$R_1$ represents hydrogen (H) or $(C_1$-$C_2)$-alkyl;
$R_2$ represents H or cyano (CN);
$R_3$ represents $CH_3$ or chlorine (Cl);
$A_1$ represents CH or nitrogen (N)
with the proviso that the two compounds characterized by the following combinations are excluded:

| $Z^1$ | $Z^2$ | $Z^3$ | $R^1$ | $A^1$ | $R^3$ | $R^2$ |
|---|---|---|---|---|---|---|
| —$CF_3$ | —S(O)—$CH_3$ | —$CH_3$ | —H | C—H | —Cl | —CN |
| —$CF_2CF_3$ | —S—$CH_3$ | —$CH_3$ | —H | C—H | —Cl | —CN |

In one preferred embodiment, in a compound of formula (I) $A_1$ is CH (while all other substituents are as defined above).

DETAILED DESCRIPTION OF A PREFERRED EMBODIMENT

In another preferred embodiment, in a compound of formula (I) $A_1$ is CH and $R_3$ is Cl (while all other substituents are as defined above).

In yet another preferred embodiment, in a compound of formula (I)
$Z_1$ is $CF_3$ or $C_2F_5$;
$Z_2$ is —S—$CH_3$—S—$C_2H_5$, —S—$CF_3$, —S—$CH_2$—$CF_3$, —SO—$CH_3$, $SO_2$—$CH_3$, —SO—$C_2H_5$ or —$SO_2$—$C_2H_5$;
$Z_3$ is $CH_3$ (while all other substituents are as defined above).

In yet another preferred embodiment, in a compound of formula (I)
$Z_1$ is $CF_3$ or $C_2F_5$;
$Z_2$ is —S—$CH_2CF_3$, —SO—$CH_2CF_3$, or $SO_2$—$CH_2CF_3$; and
$Z_3$ is $CH_3$ (while all other substituents are as defined above).

In yet another preferred embodiment, in a compound of formula (I) $R_1$ is H (while all other substituents are as defined above).

In yet another preferred embodiment, in a compound of formula (I) $A_1$ is N (while $Z_1$, $Z_2$, $Z_3$, $R_1$, $R_2$, and $R_3$ are as defined above).

In yet another preferred embodiment, in a compound of formula (I) $R_3$ is Cl.

Another aspect refers to the use of a compound of the present invention for controlling insects, arachnids and nematodes.

Yet another aspect refers to a pharmaceutical composition comprising at least one compound of the present invention.

Yet another aspect refers to a compound of the present invention for use as a medicament.

Yet another aspect refers to the use of a compound of the present invention for preparing a pharmaceutical composition for controlling parasites on animals.

Yet another aspect refers to a process for preparing a crop protection composition comprising a compound of the present invention and customary extenders and/or surfactants.

Yet another aspect refers to a compound selected from the group consisting of compounds (12), (13), (14) or (15) as described herein.

Yet another aspect refers to a process for hetepreparation of a compound of formula (I) comprising the steps of preparing compounds of formula (12), (13), (14) and (15) as described herein.

Yet another aspect refers to a method for controlling pests, characterized in that a compound of the present invention is allowed to act on the pests and/or their habitat.

Yet another aspect refers to the use of a compound of the present invention for protecting the propagation material of plants.

Definitions

According to the invention, "alkyl"—on its own or as part of a chemical group—represents straight-chain or branched hydrocarbons preferably having 1 to 6 carbon atoms such as, methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preference is furthermore given to alkyl groups having 1 to 2 carbon atoms.

According to the invention, "halogen" or "halo" represents fluorine, chlorine, bromine or iodine, in particular fluorine, chlorine or bromine.

The halogen-substituted chemical groups according to the invention such as, for example, haloalkyl are mono- or polysubstituted by halogen up to the maximum possible number of substituents (perhalogenated). In the case of polysubstitution by halogen, the halogen atoms can be identical or different, and can all be attached to one or to a plurality of carbon atoms. Here, halogen represents in particular fluorine, chlorine, bromine or iodine, preferably fluorine, chlorine or bromine and particularly preferably fluorine.

According to the invention, "halogenalkyl" represents halogen-substituted alkyl having preferably 1 to 5 identical or different halogen atoms such as, for example, monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$.

The compounds according to the invention may, depending on the nature of the substituents, be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixture of these isomers.

If appropriate, the compounds according to the invention may be present in various polymorphic forms or as a mixture of different polymorphic forms. Both the pure polymorphs and the polymorph mixtures are provided by the invention and can be used in accordance with the invention.

DETAILED DESCRIPTION

The halogen-substituted compounds according to the invention are defined by the general formula (I)

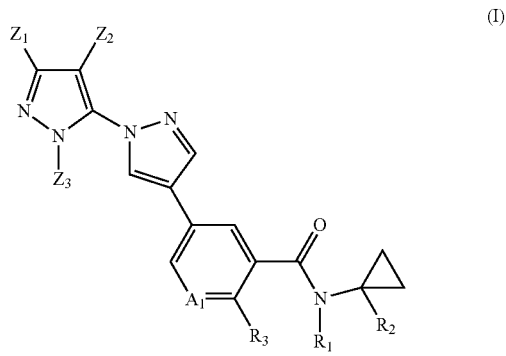

in which $Z_1$ represents perhalogenated $(C_1$-$C_2)$-alkyl, preferably $CF_3$ or $C_2F_5$;

$Z_2$ represents $—S(O)_{0-2}—(C_1$-$C_2)$-alkyl or $—S(O)_{0-2}—(C_1$-$C_2)$-halogenalkyl, preferably $—S(O)_{0-2}—CH_3$, $—S(O)_{0-2}—C_2H_5$ or $—S(O)_{0-2}—CH_2—CF_3$;

$Z_3$ represents $(C_1$-$C_2)$-alkyl, preferably $CH_3$;

$R_1$ represents hydrogen (H) or $(C_1$-$C_2)$-alkyl, preferably H or $CH_3$, more preferably H;

$R_2$ represents H or cyano (CN);

$R_3$ represents $CH_3$ or chlorine (Cl); and $A_1$ represents CH or nitrogen (N)

with the proviso that the two compounds characterized by the following combinations are excluded:

| $Z^1$ | $Z^2$ | $Z^3$ | $R^1$ | $A^1$ | $R^3$ | $R^2$ |
|---|---|---|---|---|---|---|
| —$CF_3$ | —S(O)—$CH_3$ | —$CH_3$ | —H | C—H | —Cl | —CN |
| —$CF_2CF_3$ | —S—$CH_3$ | —$CH_3$ | —H | C—H | —Cl | —CN |

In the following preferred embodiments any substituent $R_1$ to $R_3$, $A_1$, $Z_1$ to $Z_3$ of compounds of formula (I) has the meaning as defined above if not defined otherwise in the preferred embodiment. The skilled person understands that preferred embodiments can be combined as long as the combination is not against existing natural laws.

In one preferred embodiment $A_1$ is CH.

In another preferred embodiment $A_1$ is CH and $R_3$ is Cl.

In another preferred embodiment $Z_3$ is $CH_3$.

In another preferred embodiment $Z_2$ is $—S—CH_3$, $—SO—CH_3$, $—SO_2—CH_3$, $—S—C_2H_5$, $—SO—C_2H_5$, $—SO_2—C_2H_5$, $—S—CF_3$, $—SO—CF_3$, $—SO_2—CF_3$, $—S—CH_2—CF_3$, $—SO—CH_2—CF_3$, or $—SO_2—CH_2—CF_3$.

In another preferred embodiment $Z_2$ is $—S—CH_3$, $—SO—CH_3$, $—SO_2—CH_3$, $—S—C_2H_5$, $—S—CH_2—CF_3$, $—SO—CH_2—CF_3$, or $—SO_2—CH_2—CF_3$.

In another preferred embodiment $Z_2$ is —S—CH$_3$—S—C$_2$H$_5$, —SO—CH$_3$, —SO$_2$—CH$_3$.

In another preferred embodiment $Z_2$ is —S—CH$_3$, —SO—CH$_3$, —SO$_2$—CH$_3$.

In another preferred embodiment $Z_2$ is —S—CF$_3$, —SO—CF$_3$, —SO$_2$—CF$_3$, —S—CH$_2$CF$_3$, —SO—CH$_2$CF$_3$, —SO$_2$—CH$_2$CF$_3$.

In another preferred embodiment $Z_2$ is —S—CH$_2$CF$_3$, —SO—CH$_2$CF$_3$, —SO$_2$—CH$_2$CF$_3$.

In another preferred embodiment $Z_1$ is CF$_3$ or C$_2$F$_5$.

In another preferred embodiment
$Z_1$ is CF$_3$ or C$_2$F$_5$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.

In another preferred embodiment
$Z_1$ is CF$_3$ or C$_2$F$_5$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and $Z_3$ is CH$_3$.

In another preferred embodiment
$Z_1$ is CF$_3$ or C$_2$F$_5$,
$Z_2$ is —S—CH$_3$—S—C$_2$H$_5$, —SO—CH$_3$, —SO$_2$—CH$_3$, and
$Z_3$ is CH$_3$.

In another preferred embodiment
$Z_1$ is CF$_3$ or C$_2$F$_5$,
$Z_2$ is —S—CH$_3$, —SO—CH$_3$, —SO$_2$—CH$_3$, and
$Z_3$ is CH$_3$.

In another preferred embodiment
$Z_1$ is CF$_3$ or C$_2$F$_5$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.

In another preferred embodiment
$Z_1$ is CF$_3$ or C$_2$F$_5$,
$Z_2$ is, and —S—CH$_2$CF$_3$, —SO—CH$_2$CF$_3$, —SO$_2$—CH$_2$CF$_3$
$Z_3$ is CH$_3$.

In another preferred embodiment
Z is C$_2$F$_5$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.

In another preferred embodiment
$Z_1$ is C$_2$F$_5$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.

In another preferred embodiment
$Z_1$ is C$_2$F$_5$,
$Z_2$ is —S—CH$_3$—S—C$_2$H$_5$, —SO—CH$_3$, —SO$_2$—CH$_3$, and
$Z_3$ is CH$_3$.

In another preferred embodiment
$Z_1$ is C$_2$F$_5$,
$Z_2$ is —S—CH$_3$, —SO—CH$_3$, —SO$_2$—CH$_3$, and
$Z_3$ is CH$_3$.

In another preferred embodiment
$Z_1$ is C$_2$F$_5$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.

In another preferred embodiment
$Z_1$ is C$_2$F$_5$,
$Z_2$ is, and —S—CH$_2$CF$_3$, —SO—CH$_2$CF$_3$, —SO$_2$—CH$_2$CF$_3$
$Z_3$ is CH$_3$.

In another preferred embodiment
$Z_1$ is CF$_3$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.

In another preferred embodiment
$Z_1$ is CF$_3$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.

In another preferred embodiment
$Z_1$ is CF$_3$,
$Z_2$ is —S—CH$_3$—S—C$_2$H$_5$, —SO—CH$_3$, —SO$_2$—CH$_3$, and
$Z_3$ is CH$_3$.

In another preferred embodiment
$Z_1$ is CF$_3$,
$Z_2$ is —S—CH$_3$, —SO—CH$_3$, —SO$_2$—CH$_3$, and
$Z_3$ is CH$_3$.

In another preferred embodiment
$Z_1$ is CF$_3$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.

In another preferred embodiment
$Z_1$ is CF$_3$,
$Z_2$ is, and —S—CH$_2$CF$_3$, —SO—CH$_2$CF$_3$, —SO$_2$—CH$_2$CF$_3$
$Z_3$ is CH$_3$.

In another preferred embodiment
$A_1$ is CH,
$R_3$ is Cl,
$Z_1$ is CF$_3$ or C$_2$F$_5$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.

In another preferred embodiment
$A_1$ is CH,
$R_3$ is Cl,
$Z_1$ is CF$_3$ or C$_2$F$_5$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.

In another preferred embodiment
$A_1$ is CH,
$R_3$ is Cl,
$Z_1$ is CF$_3$ or C$_2$F$_5$,
$Z_2$ is —S—CH$_3$—S—C$_2$H$_5$, —SO—CH$_3$, —SO$_2$—CH$_3$, and
$Z_3$ is CH$_3$.

In another preferred embodiment
$A_1$ is CH,
$R_3$ is Cl,
$Z_1$ is CF$_3$ or C$_2$F$_5$,
$Z_2$ is —S—CH$_3$, —SO—CH$_3$, —SO$_2$—CH$_3$, and
$Z_3$ is CH$_3$.

In another preferred embodiment
$A_1$ is CH,
$R_3$ is Cl,
$Z_1$ is $CF_3$ or $C_2F_5$,
$Z_2$ is, and $-S-CF_3$, $-SO-CF_3$, $-SO_2-CF_3$, $-S-CH_2CF_3$, $-SO-CH_2CF_3$, $-SO_2-CH_2CF_3$
$Z_3$ is $CH_3$.

In another preferred embodiment
$A_1$ is CH,
$R_3$ is Cl,
$Z_1$ is $CF_3$ or $C_2F_5$,
$Z_2$ is, and $-S-CH_2CF_3$, $-SO-CH_2CF_3$, $-SO_2-CH_2CF_3$
$Z_3$ is $CH_3$.

In another preferred embodiment
$A_1$ is CH,
$R_3$ is Cl,
$Z_1$ is $C_2F_5$,
$Z_2$ is $-S-CH_3$, $-SO-CH_3$, $-SO_2-CH_3$, $-S-C_2H_5$, $-SO-C_2H_5$, $-SO_2-C_2H_5$, $-S-CF_3$, $-SO-CF_3$, $-SO_2-CF_3$, $-S-CH_2-CF_3$, $-SO-CH_2-CF_3$, or $-SO_2-CH_2-CF_3$, and
$Z_3$ is $CH_3$.

In another preferred embodiment
$A_1$ is CH,
$R_3$ is Cl,
$Z_1$ is $C_2F_5$,
$Z_2$ is $-S-CH_3$, $-SO-CH_3$, $-SO_2-CH_3$, $-S-C_2H_5$, $-S-CH_2-CF_3$, $-SO-CH_2-CF_3$, or $-SO_2-CH_2-CF_3$, and
$Z_3$ is $CH_3$.

In another preferred embodiment
$A_1$ is CH,
$R_3$ is Cl,
$Z_1$ is $C_2F_5$,
$Z_2$ is $-S-CH_3-S-C_2H_5$, $-SO-CH_3$, $-SO_2-CH_3$, and
$Z_3$ is $CH_3$.

In another preferred embodiment
$A_1$ is CH,
$R_3$ is Cl,
$Z_1$ is $C_2F_5$,
$Z_2$ is $-S-CH_3$, $-SO-CH_3$, $-SO_2-CH_3$, and
$Z_3$ is $CH_3$.

In another preferred embodiment
$A_1$ is CH,
$R_3$ is Cl,
$Z_1$ is $C_2F_5$,
$Z_2$ is, and $-S-CF_3$, $-SO-CF_3$, $-SO_2-CF_3$, $-S-CH_2CF_3$, $-SO-CH_2CF_3$, $-SO_2-CH_2CF_3$
$Z_3$ is $CH_3$.

In another preferred embodiment
$A_1$ is CH,
$R_3$ is Cl,
$Z_1$ is $C_2F_5$,
$Z_2$ is, and $-S-CH_2CF_3$, $-SO-CH_2CF_3$, $-SO_2-CH_2CF_3$
$Z_3$ is $CH_3$.

In another preferred embodiment
$A_1$ is CH,
$R_3$ is Cl,
$Z_1$ is $CF_3$,
$Z_2$ is $-S-CH_3$, $-SO-CH_3$, $-SO_2-CH_3$, $-S-C_2H_5$, $-SO-C_2H_5$, $-SO_2-C_2H_5$, $-S-CF_3$, $-SO-CF_3$, $-SO_2-CF_3$, $-S-CH_2-CF_3$, $-SO-CH_2-CF_3$, or $-SO_2-CH_2-CF_3$, and
$Z_3$ is $CH_3$.

In another preferred embodiment
$A_1$ is CH,
$R_3$ is Cl,
$Z_1$ is $CF_3$,
$Z_2$ is $-S-CH_3$, $-SO-CH_3$, $-SO_2-CH_3$, $-S-C_2H_5$, $-S-CH_2-CF_3$, $-SO-CH_2-CF_3$, or $-SO_2-CH_2-CF_3$, and
$Z_3$ is $CH_3$.

In another preferred embodiment
$A_1$ is CH,
$R_3$ is Cl,
$Z_1$ is $CF_3$,
$Z_2$ is $-S-CH_3-S-C_2H_5$, $-SO-CH_3$, $-SO_2-CH_3$, and
$Z_3$ is $CH_3$.

In another preferred embodiment
$A_1$ is CH,
$R_3$ is Cl,
$Z_1$ is $CF_3$,
$Z_2$ is $-S-CH_3$, $-SO-CH_3$, $-SO_2-CH_3$, and
$Z_3$ is $CH_3$.

In another preferred embodiment
$A_1$ is CH,
$R_3$ is Cl,
$Z_1$ is $CF_3$,
$Z_2$ is, and $-S-CF_3$, $-SO-CF_3$, $-SO_2-CF_3$, $-S-CH_2CF_3$, $-SO-CH_2CF_3$, $-SO_2-CH_2CF_3$
$Z_3$ is $CH_3$.

In another preferred embodiment
$A_1$ is CH,
$R_3$ is Cl,
$Z_1$ is $CF_3$,
$Z_2$ is, and $-S-CH_2CF_3$, $-SO-CH_2CF_3$, $-SO_2-CH_2CF_3$
$Z_3$ is $CH_3$.

In another preferred embodiment, $R_1$ is H or $CH_3$.
In another preferred embodiment, $R_1$ is H.
In another preferred embodiment
$A_1$ is CH,
$R_1$ is H,
$R_3$ is Cl,
$Z_1$ is $CF_3$ or $C_2F_5$,
$Z_2$ is $-S-CH_3$, $-SO-CH_3$, $-SO_2-CH_3$, $-S-C_2H_5$, $-SO-C_2H_5$, $-SO_2-C_2H_5$, $-S-CF_3$, $-SO-CF_3$, $-SO_2-CF_3$, $-S-CH_2-CF_3$, $-SO-CH_2-CF_3$, or $-SO_2-CH_2-CF_3$, and
$Z_3$ is $CH_3$.

In another preferred embodiment
$A_1$ is CH,
$R_1$ is H,
$R_3$ is Cl,
$Z_1$ is $CF_3$ or $C_2F_5$,
$Z_2$ is $-S-CH_3$, $-SO-CH_3$, $-SO_2-CH_3$, $-S-C_2H_5$, $-S-CH_2-CF_3$, $-SO-CH_2-CF_3$, or $-SO_2-CH_2-CF_3$, and
$Z_3$ is $CH_3$.

In another preferred embodiment
$A_1$ is CH,
$R_1$ is H,
$R_3$ is Cl,
$Z_1$ is $CF_3$ or $C_2F_5$,
$Z_2$ is $-S-CH_3-S-C_2H_5$, $-SO-CH_3$, $-SO_2-CH_3$, and
$Z_3$ is $CH_3$.

In another preferred embodiment
$A_1$ is CH,
$R_1$ is H, $R_3$ is Cl,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_3$ is Cl,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_3$ is Cl,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_3$ is Cl,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_3$ is Cl,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_3$ is Cl,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_3$ is Cl,
$Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_3$ is Cl,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_3$ is Cl,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_3$ is Cl,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_3$ is Cl,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_3$ is Cl,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_3$ is Cl,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment $R_1$ is $CH_3$.
In another preferred embodiment
$A_1$ is CH,
$R_1$ is $CH_3$,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$R_1$ is $CH_3$,
$R_3$ is Cl, $Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_3$ is Cl,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_3$ is Cl,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_3$ is Cl,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_3$ is Cl,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$R_1$ is $CH_3$,
$R_3$ is Cl,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_3$ is Cl,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_3$ is Cl,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_3$ is Cl,
$Z_1$ is $C_2F_5$, $Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_3$ is Cl,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_3$ is Cl,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_3$ is Cl,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_3$ is Cl,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_3$ is Cl,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_3$ is Cl,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_3$ is Cl,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_3$ is Cl,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.

In another preferred embodiment $A_1$ is N.
In another preferred embodiment
$A_1$ is N,
$R_1$ is H,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_3$ is Cl,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is H,
$R_3$ is Cl,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is H,
$R_3$ is Cl,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_3$ is Cl,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_3$ is Cl,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_3$ is Cl,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_3$ is Cl,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is H,
$R_3$ is Cl,
$Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is H,
$R_3$ is Cl,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_3$ is Cl,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_3$ is Cl,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is H,
$R_3$ is Cl,
$Z_1$ is $CF_3$, $Z_2$ is —S—CH$_3$, —SO—CH$_3$, —SO$_2$—CH$_3$, and
$Z_3$ is CH$_3$.
In another preferred embodiment
$A_1$ is N,
$R_1$ is H,
$R_3$ is Cl,
$Z_1$ is CF$_3$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.
In another preferred embodiment
$A_1$ is N,
$R_1$ is H,
$R_3$ is Cl,
$Z_1$ is CF$_3$,
$Z_2$ is, and —S—CH$_2$CF$_3$, —SO—CH$_2$CF$_3$, —SO$_2$—CH$_2$CF$_3$
$Z_3$ is CH$_3$.
In another preferred embodiment
$A_1$ is N,
$R_1$ is CH$_3$,
$R_3$ is Cl,
$Z_1$ is CF$_3$ or C$_2$F$_5$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is N,
$R_1$ is CH$_3$,
$R_3$ is Cl,
$Z_1$ is CF$_3$ or C$_2$F$_5$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is N,
$R_1$ is CH$_3$,
$R_3$ is Cl,
$Z_1$ is CF$_3$ or C$_2$F$_5$,
$Z_2$ is —S—CH$_3$—S—C$_2$H$_5$, —SO—CH$_3$, —SO$_2$—CH$_3$, and
$Z_3$ is CH$_3$.
In another preferred embodiment
$A_1$ is N,
$R_1$ is CH$_3$,
$R_3$ is Cl,
$Z_1$ is CF$_3$ or C$_2$F$_5$,
$Z_2$ is —S—CH$_3$, —SO—CH$_3$, —SO$_2$—CH$_3$, and
$Z_3$ is CH$_3$.
In another preferred embodiment
$A_1$ is N,
$R_1$ is CH$_3$,
$R_3$ is Cl,
$Z_1$ is CF$_3$ or C$_2$F$_5$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.
In another preferred embodiment
$A_1$ is N,
$R_1$ is CH$_3$,
$R_3$ is Cl,
$Z_1$ is CF$_3$ or C$_2$F$_5$,
$Z_2$ is, and —S—CH$_2$CF$_3$, —SO—CH$_2$CF$_3$, —SO$_2$—CH$_2$CF$_3$
$Z_3$ is CH$_3$.
In another preferred embodiment
$A_1$ is N,
$R_1$ is CH$_3$,
$R_3$ is Cl,
$Z_1$ is C$_2$F$_5$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is N,
$R_1$ is CH$_3$,
$R_3$ is Cl,
$Z_1$ is C$_2$F$_5$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is N,
$R_1$ is CH$_3$,
$R_3$ is Cl,
$Z_1$ is C$_2$F$_5$,
$Z_2$ is —S—CH$_3$—S—C$_2$H$_5$, —SO—CH$_3$, —SO$_2$—CH$_3$, and
$Z_3$ is CH$_3$.
In another preferred embodiment
$A_1$ is N,
$R_1$ is CH$_3$,
$R_3$ is Cl,
$Z_1$ is C$_2$F$_5$,
$Z_2$ is —S—CH$_3$, —SO—CH$_3$, —SO$_2$—CH$_3$, and
$Z_3$ is CH$_3$.
In another preferred embodiment
$A_1$ is N,
$R_1$ is CH$_3$,
$R_3$ is Cl,
$Z_1$ is C$_2$F$_5$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.
In another preferred embodiment
$A_1$ is N,
$R_1$ is CH$_3$,
$R_3$ is Cl,
$Z_1$ is C$_2$F$_5$,
$Z_2$ is, and —S—CH$_2$CF$_3$, —SO—CH$_2$CF$_3$, —SO$_2$—CH$_2$CF$_3$
$Z_3$ is CH$_3$.
In another preferred embodiment
$A_1$ is N,
$R_1$ is CH$_3$,
$R_3$ is Cl,
$Z_1$ is CF$_3$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is N,
$R_1$ is CH$_3$,
$R_3$ is Cl,
$Z_1$ is CF$_3$, $Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_3$ is Cl,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_3$ is Cl,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_3$ is Cl,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_3$ is Cl,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment $R_2$ is H.
In another preferred embodiment, $R_2$ is H and $R_1$ is H or $CH_3$.
In another preferred embodiment, $R_2$ is H and $R_1$ is H.
In another preferred embodiment
$R_1$ is H,
$R_2$ is H,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is H,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is H,
$R_3$ is Cl,
$Z_1$ is $CF_3$ or $C_2F_5$, $Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_2$ is H,
$R_3$ is Cl,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_2$ is H,
$R_3$ is Cl,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is H,
$R_3$ is Cl,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is H,
$R_3$ is Cl,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is H,
$R_3$ is Cl,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is H,
$R_3$ is Cl,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_2$ is H,
$R_3$ is Cl,
$Z_1$ is $C_2F_5$,
$Z_2$ is —S—$CH_3$, —SO—$CH_3$, —$SO_2$—$CH_3$, and
$Z_3$ is $CH_3$.

In another preferred embodiment
$A_1$ is CH,
$R_1$ is H,
$R_2$ is H,
$R_3$ is Cl,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is H,
$R_3$ is Cl,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is H,
$R_3$ is Cl,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_2$ is H,
$R_3$ is Cl,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_2$ is H,
$R_3$ is Cl,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is CH,
$R_1$ is H,
$R_2$ is H,
$R_3$ is Cl,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment $R_2$ is H and $R_1$ is $CH_3$.
In another preferred embodiment
$A_1$ is CH,
$R_1$ is $CH_3$,
$R_2$ is H,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is H,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and $Z_3$ is $CH_3$.
In another preferred embodiment
$A_1$ is CH,
$R_1$ is $CH_3$,
$R_2$ is H,
$R_3$ is Cl,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is Cl,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is Cl,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is H,
$R_3$ is Cl,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is H, $R_3$ is Cl,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is H,
$R_3$ is Cl,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is H,
$R_3$ is Cl,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is Cl,
$Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is Cl,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is H,
$R_3$ is Cl,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is H,
$R_3$ is Cl,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is Cl,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is Cl,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is H,
$R_3$ is Cl,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment $R_2$ is H and $A_1$ is N.
In another preferred embodiment
$A_1$ is N,
$R_1$ is H,
$R_2$ is H,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_2$ is H,
$R_3$ is Cl,
$Z_1$ is $CF_3$ or $C_2F$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_2$ is H, $R_3$ is Cl,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is H,
$R_2$ is H,
$R_3$ is Cl,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_5$ is H,
$R_2$ is H,
$R_3$ is Cl,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_2$ is H,
$R_3$ is Cl,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_2$ is H,
$R_3$ is Cl,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_2$ is H,
$R_3$ is Cl,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_2$ is H,
$R_3$ is Cl,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is H,
$R_2$ is H,
$R_3$ is Cl,
$Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is H,
$R_2$ is H,
$R_3$ is Cl,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_2$ is H,
$R_3$ is Cl,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_2$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_2$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_2$ is H,
$R_3$ is Cl,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is H,
$R_2$ is H,
$R_3$ is Cl,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is H,
$R_2$ is H,
$R_3$ is Cl,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is H,
$R_2$ is H,
$R_3$ is Cl,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is $CH_3$,
$R_2$ is H,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is $CH_3$,
$R_2$ is H,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is $CH_3$,
$R_2$ is H,
$R_3$ is Cl,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.

In another preferred embodiment
$A_1$ is N,
$R_1$ is $CH_3$,
$R_2$ is H,
$R_3$ is Cl,
$Z_1$ is $CF_3$ or $C_2F_5$,
$Z_2$ is —S—$CH_3$, —SO—$CH_3$, —$SO_2$—$CH_3$, and
$Z_3$ is $CH_3$.

In another preferred embodiment
$A_1$ is N,
$R_1$ is $CH_3$,
$R_2$ is H,
$R_3$ is Cl,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is $CH_3$,
$R_2$ is H,
$R_3$ is Cl,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is $CH_3$,
$R_2$ is H,
$R_3$ is Cl,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is $CH_3$,
$R_2$ is H,
$R_3$ is Cl,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is $CH_3$,
$R_2$ is H,
$R_3$ is Cl,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.

In another preferred embodiment
$A_1$ is N,
$R_1$ is $CH_3$,
$R_2$ is H,
$R_3$ is Cl,
$Z_1$ is $C_2F_5$,
$Z_2$ is —S—$CH_3$, —SO—$CH_3$, —$SO_2$—$CH_3$, and
$Z_3$ is $CH_3$.

In another preferred embodiment
$A_1$ is N,
$R_1$ is $CH_3$,
$R_2$ is H,
$R_3$ is Cl,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is $CH_3$,
$R_2$ is H,
$R_3$ is Cl,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is $CH_3$,
$R_2$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is $CH_3$,
$R_2$ is H,
$R_3$ is Cl,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is H,
$R_3$ is Cl,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_2$ is H,
$R_3$ is Cl,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_2$ is H,
$R_3$ is Cl,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is H,
$R_3$ is Cl,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment $R_2$ is CN.
In another preferred embodiment, $R_2$ is CN and $R_1$ is H or $CH_3$.
In another preferred embodiment, $R_2$ is CN and $R_1$ is H.
In another preferred embodiment
$A_1$ is CH,
$R_1$ is H,
$R_2$ is CN,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$, is CH,
$R_1$ is H,
$R_2$ is CN,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is CN,
$R_3$ is Cl,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_2$ is CN,
$R_3$ is Cl,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_2$ is CN,
$R_3$ is Cl,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is CN,
$R_3$ is Cl,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is CN,
$R_3$ is Cl,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is CN,
$R_3$ is Cl,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is CN,
$R_3$ is Cl,
$Z_1$ is $C_2F_5$, $Z_2$ is —S—CH$_3$—S—C$_2$H$_5$, —SO—CH$_3$, —SO$_2$—CH$_3$, and
$Z_3$ is CH$_3$.
In another preferred embodiment
$A_1$ is CH,
$R_1$ is H,
$R_2$ is CN,
$R_3$ is Cl,
$Z_1$ is C$_2$F$_5$,
$Z_2$ is —S—CH$_3$, —SO—CH$_3$, —SO$_2$—CH$_3$, and
$Z_3$ is CH$_3$.
In another preferred embodiment
$A_1$ is CH,
$R_1$ is H,
$R_2$ is CN,
$R_3$ is Cl,
$Z_1$ is C$_2$F$_5$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.
In another preferred embodiment
$A_1$ is CH,
$R_1$ is H,
$R_2$ is CN,
$R_3$ is Cl,
$Z_1$ is C$_2$F$_5$,
$Z_2$ is, and —S—CH$_2$CF$_3$, —SO—CH$_2$CF$_3$, —SO$_2$—CH$_2$CF$_3$
$Z_3$ is CH$_3$.
In another preferred embodiment
$A_1$ is CH,
$R_1$ is H,
$R_2$ is CN,
$R_3$ is Cl,
$Z_1$ is CF$_3$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_1$ is H,
$R_2$ is CN,
$R_3$ is Cl,
$Z_1$ is CF$_3$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_1$ is H,
$R_2$ is CN,
$R_3$ is Cl,
$Z_1$ is CF$_3$,
$Z_2$ is —S—CH$_3$—S—C$_2$H$_5$, —SO—CH$_3$, —SO$_2$—CH$_3$, and
$Z_3$ is CH$_3$.
In another preferred embodiment
$A_1$ is CH,
$R_1$ is H,
$R_2$ is CN,
$R_3$ is Cl,
$Z_1$ is CF$_3$,
$Z_2$ is —S—CH$_3$, —SO—CH$_3$, —SO$_2$—CH$_3$, and
$Z_3$ is CH$_3$.

In another preferred embodiment
$A_1$ is CH,
$R_1$ is H,
$R_2$ is CN,
$R_3$ is Cl,
$Z_1$ is CF$_3$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.
In another preferred embodiment
$R_1$ is H,
$R_2$ is CN,
$R_3$ is Cl,
$Z_1$ is CF$_3$,
$Z_2$ is, and —S—CH$_2$CF$_3$, —SO—CH$_2$CF$_3$, —SO$_2$—CH$_2$CF$_3$
$Z_3$ is CH$_3$.
In another preferred embodiment $R_2$ is CN and $R_1$ is CH$_3$.
In another preferred embodiment
$A_1$ is CH,
$R_1$ is CH$_3$,
$R_2$ is CN,
$R_3$ is Cl,
$Z_1$ is CF$_3$ or C$_2$F$_5$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_1$ is CH$_3$,
$R_2$ is CN,
$R_3$ is Cl,
$Z_1$ is CF$_3$ or C$_2$F$_5$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_1$ is CH$_3$,
$R_2$ is CN,
$R_3$ is Cl,
$Z_1$ is CF$_3$ or C$_2$F$_5$,
$Z_2$ is —S—CH$_3$—S—C$_2$H$_5$, —SO—CH$_3$, —SO$_2$—CH$_3$, and
$Z_3$ is CH$_3$.
In another preferred embodiment
$A_1$ is CH,
$R_1$ is CH$_3$,
$R_2$ is CN,
$R_3$ is Cl,
$Z_1$ is CF$_3$ or C$_2$F$_5$,
$Z_2$ is —S—CH$_3$, —SO—CH$_3$, —SO$_2$—CH$_3$, and
$Z_3$ is CH$_3$.
In another preferred embodiment
$A_1$ is CH,
$R_1$ is CH$_3$,
$R_2$ is CN,
$R_3$ is Cl,
$Z_1$ is CF$_3$ or C$_2$F$_5$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.

In another preferred embodiment
$A_1$ is CH,
$R_1$ is $CH_3$,
$R_2$ is CN,
$R_3$ is Cl,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is CH,
$R_1$ is $CH_3$,
$R_2$ is CN,
$R_3$ is Cl,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is CH,
$R_1$ is $CH_3$,
$R_2$ is CN,
$R_3$ is Cl,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is CH,
$R_1$ is $CH_3$,
$R_2$ is CN,
$R_3$ is Cl,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.

In another preferred embodiment
$A_1$ is CH,
$R_1$ is $CH_3$,
$R_2$ is CN,
$R_3$ is Cl,
$Z_1$ is $C_2F_5$,
$Z_2$ is —S—$CH_3$, —SO—$CH_3$, —$SO_2$—$CH_3$, and
$Z_3$ is $CH_3$.

In another preferred embodiment
$A_1$ is CH,
$R_1$ is $CH_3$,
$R_2$ is CN,
$R_3$ is Cl,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is CH,
$R_1$ is $CH_3$,
$R_2$ is CN,
$R_3$ is Cl,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is CH,
$R_1$ is $CH_3$,
$R_2$ is CN,
$R_3$ is Cl,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is CH,
$R_1$ is $CH_3$,
$R_2$ is CN,
$R_3$ is Cl,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is CH,
$R_1$ is $CH_3$,
$R_2$ is CN,
$R_3$ is Cl,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.

In another preferred embodiment
$A_1$ is CH,
$R_1$ is $CH_3$,
$R_2$ is CN,
$R_3$ is Cl,
$Z_1$ is $CF_3$,
$Z_2$ is —S—$CH_3$, —SO—$CH_3$, —$SO_2$—$CH_3$, and
$Z_3$ is $CH_3$.

In another preferred embodiment
$R_1$ is $CH_3$,
$R_2$ is CN,
$R_3$ is Cl,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is CH,
$R_1$ is $CH_3$,
$R_2$ is CN,
$R_3$ is Cl,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.

In another preferred embodiment $R_2$ is CN and $A_1$ is N.

In another preferred embodiment
$A_1$ is N,
$R_1$ is H,
$R_2$ is CN,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is H,
$R_2$ is CN,
$R_3$ is Cl,
$Z_1$ is $CF_3$ or $C_2F_5$,
$Z_2$ is $-S-CH_3$, $-SO-CH_3$, $-SO_2-CH_3$, $-S-C_2H_5$, $-S-CH_2-CF_3$, $-SO-CH_2-CF_3$, or $-SO_2-CH_2-CF_3$, and
$Z_3$ is $CH_3$.

In another preferred embodiment
$A_1$ is N,
$R_1$ is H,
$R_2$ is CN,
$R_3$ is Cl,
$Z_1$ is $CF_3$ or $C_2F_5$,
$Z_2$ is $-S-CH_3-S-C_2H_5$, $-SO-CH_3$, $-SO_2-CH_3$, and
$Z_3$ is $CH_3$.

In another preferred embodiment
$A_1$ is N,
$R_1$ is H,
$R_2$ is CN,
$R_3$ is Cl,
$Z_1$ is $CF_3$ or $C_2F_5$,
$Z_2$ is $-S-CH_3$, $-SO-CH_3$, $-SO_2-CH_3$, and
$Z_3$ is $CH_3$.

In another preferred embodiment
$A_1$ is N,
$R_1$ is H,
$R_2$ is CN,
$R_3$ is Cl,
$Z_1$ is $CF_3$ or $C_2F_5$,
$Z_2$ is, and $-S-CF_3$, $-SO-CF_3$, $-SO_2-CF_3$, $-S-CH_2CF_3$, $-SO-CH_2CF_3$, $-SO_2-CH_2CF_3$
$Z_3$ is $CH_3$.

In another preferred embodiment
$A_1$ is N,
$R_1$ is H,
$R_2$ is CN,
$R_3$ is Cl,
$Z_1$ is $CF_3$ or $C_2F_5$,
$Z_2$ is, and $-S-CH_2CF_3$, $-SO-CH_2CF_3$, $-SO_2-CH_2CF_3$
$Z_3$ is $CH_3$.

In another preferred embodiment
$A_1$ is N,
$R_1$ is H,
$R_2$ is CN,
$R_3$ is Cl,
$Z_1$ is $C_2F_5$,
$Z_2$ is $-S-CH_3$, $-SO-CH_3$, $-SO_2-CH_3$, $-S-C_2H_5$, $-SO-C_2H_5$, $-SO_2-C_2H_5$, $-S-CF_3$, $-SO-CF_3$, $-SO_2-CF_3$, $-S-CH_2-CF_3$, $-SO-CH_2-CF_3$, or $-SO_2-CH_2-CF_3$, and
$Z_3$ is $CH_3$.

In another preferred embodiment
$A_1$ is N,
$R_1$ is H,
$R_2$ is CN,
$R_3$ is Cl,
$Z_1$ is $C_2F_5$,
$Z_2$ is $-S-CH_3$, $-SO-CH_3$, $-SO_2-CH_3$, $-S-C_2H_5$, $-S-CH_2-CF_3$, $-SO-CH_2-CF_3$, or $-SO_2-CH_2-CF_3$, and
$Z_3$ is $CH_3$.

In another preferred embodiment
$A_1$ is N,
$R_1$ is H,
$R_2$ is CN,
$R_3$ is Cl,
$Z_1$ is $C_2F_5$,
$Z_2$ is $-S-CH_3-S-C_2H_5$, $-SO-CH_3$, $-SO_2-CH_3$, and
$Z_3$ is $CH_3$.

In another preferred embodiment
$A_1$ is N,
$R_1$ is H,
$R_2$ is CN,
$R_3$ is Cl,
$Z_1$ is $C_2F_5$,
$Z_2$ is $-S-CH_3$, $-SO-CH_3$, $-SO_2-CH_3$, and
$Z_3$ is $CH_3$.

In another preferred embodiment
$A_1$ is N,
$R_1$ is H,
$R_2$ is CN,
$R_3$ is Cl,
$Z_1$ is $C_2F_5$,
$Z_2$ is, and $-S-CF_3$, $-SO-CF_3$, $-SO_2-CF_3$, $-S-CH_2CF_3$, $-SO-CH_2CF_3$, $-SO_2-CH_2CF_3$
$Z_3$ is $CH_3$.

In another preferred embodiment
$A_1$ is N,
$R_1$ is H,
$R_2$ is CN,
$R_3$ is Cl,
$Z_1$ is $C_2F_5$,
$Z_2$ is, and $-S-CH_2CF_3$, $-SO-CH_2CF_3$, $-SO_2-CH_2CF_3$
$Z_3$ is $CH_3$.

In another preferred embodiment
$A_1$ is N,
$R_1$ is H,
$R_2$ is CN,
$R_3$ is Cl,
$Z_1$ is $CF_3$,
$Z_2$ is $-S-CH_3$, $-SO-CH_3$, $-SO_2-CH_3$, $-S-C_2H_5$, $-SO-C_2H_5$, $-SO_2-C_2H_5$, $-S-CF_3$, $-SO-CF_3$, $-SO_2-CF_3$, $-S-CH_2-CF_3$, $-SO-CH_2-CF_3$, or $-SO_2-CH_2-CF_3$, and
$Z_3$ is $CH_3$.

In another preferred embodiment
$A_1$ is N,
$R_1$ is H,
$R_2$ is CN,
$R_3$ is Cl,
$Z_1$ is $CF_3$,
$Z_2$ is $-S-CH_3$, $-SO-CH_3$, $-SO_2-CH_3$, $-S-C_2H_5$, $-S-CH_2-CF_3$, $-SO-CH_2-CF_3$, or $-SO_2-CH_2-CF_3$, and
$Z_3$ is $CH_3$.

In another preferred embodiment
$A_1$ is N,
$R_1$ is H,
$R_2$ is CN,
$R_3$ is Cl,
$Z_1$ is $CF_3$,
$Z_2$ is $-S-CH_3-S-C_2H_5$, $-SO-CH_3$, $-SO_2-CH_3$, and
$Z_3$ is $CH_3$.

In another preferred embodiment
$A_1$ is N,
$R_1$ is H, $R_2$ is CN,
$R_3$ is Cl,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is H,
$R_2$ is CN,
$R_3$ is Cl,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_2$ is CN,
$R_3$ is Cl,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is CN,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is CN,
$R_3$ is Cl,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is CN,
$R_3$ is Cl,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_2$ is CN,
$R_3$ is Cl,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_2$ is CN,
$R_3$ is Cl,
$Z_1$ is $CF_3$ or $C_2F_5$, $Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is CN,
$R_3$ is Cl,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is CN,
$R_3$ is Cl,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is CN,
$R_3$ is Cl,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is CN,
$R_3$ is Cl,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_2$ is CN,
$R_3$ is Cl,
$Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_2$ is CN,
$R_3$ is Cl,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is CN,
$R_3$ is Cl,
$Z_1$ is $C_2F_5$, $Z_2$ is, and —S—CH$_2$CF$_3$, —SO—CH$_2$CF$_3$, —SO$_2$—CH$_2$CF$_3$
$Z_3$ is CH$_3$.
In another preferred embodiment
$A_1$ is N,
$R_1$ is CH$_3$,
$R_2$ is CN,
$R_3$ is Cl,
$Z_1$ is CF$_3$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is N,
$R_1$ is CH$_3$,
$R_2$ is CN,
$R_3$ is Cl,
$Z_1$ is CF$_3$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is N,
$R_1$ is CH$_3$,
$R_2$ is CN,
$R_3$ is Cl,
$Z_1$ is CF$_3$,
$Z_2$ is —S—CH$_3$—S—C$_2$H$_5$, —SO—CH$_3$, —SO$_2$—CH$_3$, and
$Z_3$ is CH$_3$.
In another preferred embodiment
$A_1$ is N,
$R_1$ is CH$_3$,
$R_2$ is CN,
$R_3$ is Cl,
$Z_1$ is CF$_3$,
$Z_2$ is —S—CH$_3$, —SO—CH$_3$, —SO$_2$—CH$_3$, and
$Z_3$ is CH$_3$.
In another preferred embodiment
$A_1$ is N,
$R_1$ is CH$_3$,
$R_2$ is CN,
$R_3$ is Cl,
$Z_1$ is CF$_3$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.
In another preferred embodiment
$A_1$ is N,
$R_1$ is CH$_3$,
$R_2$ is CN,
$R_3$ is Cl,
$Z_1$ is CF$_3$,
$Z_2$ is, and —S—CH$_2$CF$_3$, —SO—CH$_2$CF$_3$, —SO$_2$—CH$_2$CF$_3$
$Z_3$ is CH$_3$.
In another preferred embodiment $R_3$ is CH$_3$.
In another preferred embodiment
$A_1$ is CH,
$R_3$ is CH$_3$,
$Z_1$ is CF$_3$ or C$_2$F$_5$, $Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_3$ is CH$_3$,
$Z_1$ is CF$_3$ or C$_2$F$_5$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_3$ is CH$_3$,
$Z_1$ is CF$_3$ or C$_2$F$_5$,
$Z_2$ is —S—CH$_3$—S—C$_2$H$_5$, —SO—CH$_3$, —SO$_2$—CH$_3$, and
$Z_3$ is CH$_3$.
In another preferred embodiment
$A_1$ is CH,
$R_3$ is CH$_3$,
$Z_1$ is CF$_3$ or C$_2$F$_5$,
$Z_2$ is —S—CH$_3$, —SO—CH$_3$, —SO$_2$—CH$_3$, and
$Z_3$ is CH$_3$.
In another preferred embodiment
$A_1$ is CH,
$R_3$ is CH$_3$,
$Z_1$ is CF$_3$ or C$_2$F$_5$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.
In another preferred embodiment
$A_1$ is CH,
$R_3$ is CH$_3$,
$Z_1$ is CF$_3$ or C$_2$F$_5$,
$Z_2$ is, and —S—CH$_2$CF$_3$, —SO—CH$_2$CF$_3$, —SO$_2$—CH$_2$CF$_3$
$Z_3$ is CH$_3$.
In another preferred embodiment
$A_1$ is CH,
$R_3$ is CH$_3$,
$Z_1$ is C$_2$F$_5$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_3$ is CH$_3$,
$Z_1$ is C$_2$F$_5$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_3$ is CH$_3$,
$Z_1$ is C$_2$F$_5$,
$Z_2$ is —S—CH$_3$—S—C$_2$H$_5$, —SO—CH$_3$, —SO$_2$—CH$_3$, and
$Z_3$ is CH$_3$.
In another preferred embodiment
$A_1$ is CH,
$R_3$ is CH$_3$, $Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_3$ is $CH_3$,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$, is CH,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is CH,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment, $R_3$ is $CH_3$, $R_1$, is H or $CH_3$.
In another preferred embodiment, $R_3$ is $CH_3$, $R_1$ is H.
In another preferred embodiment
$A_1$ is CH,
$R_1$ is H,
$R_3$ is $CH_3$, $Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_3$ is $CH_3$,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_3$ is $CH_3$,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_3$ is $CH_3$,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is CH,
$R_1$ is H,
$R_3$ is $CH_3$,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_3$ is $CH_3$,
$Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_3$ is $CH_3$,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment $R_3$ is $CH_3$ and $R_1$ is $CH_3$.
In another preferred embodiment
$R_1$ is $CH_3$,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_3$ is $CH_3$,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_3$ is $CH_3$,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_3$ is $CH_3$,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_3$ is $CH_3$,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is CH,
$R_1$ is $CH_3$,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is CH,
$R_1$ is $CH_3$,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is CH,
$R_1$ is $CH_3$,
$R_3$ is $CH_3$,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.

In another preferred embodiment
$A_1$ is CH,
$R_1$ is $CH_3$,
$R_3$ is $CH_3$,
$Z_1$ is $C_2F_5$,
$Z_2$ is —S—$CH_3$, —SO—$CH_3$, —$SO_2$—$CH_3$, and
$Z_3$ is $CH_3$.

In another preferred embodiment
$A_1$ is CH,
$R_1$ is $CH_3$,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is CH,
$R_1$ is $CH_3$,
$R_3$ is $CH_3$,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is CH,
$R_1$ is $CH_3$,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is CH,
$R_1$ is $CH_3$,
$R_3$ is $CH_3$,
$Z_1$ is $CF_3$, $Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is CH,
$R_1$ is $CH_3$,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.

In another preferred embodiment
$A_1$ is CH,
$R_1$ is $CH_3$,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.

In another preferred embodiment
$A_1$ is CH,
$R_1$ is $CH_3$,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is CH,
$R_1$ is $CH_3$,
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.

In another preferred embodiment $A_1$ is N.
In another preferred embodiment
$A_1$ is N,
$R_1$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is H,
$R_3$ is $CH_3$,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.

In another preferred embodiment
$A_1$ is N,
$R_1$ is H,
$R_3$ is $CH_3$, $Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$, is N,
$R_1$ is H,
$R_3$ is $CH_3$,
$Z_1$ is $CF_3$ or $C_2F$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_3$ is $CH_3$,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_3$ is $CH_3$,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is H,
$R_3$ is $CH_3$,
$Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is H,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_3$ is $CH_3$,
$Z_1$ is $C_2F_5$, $Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is H,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is H,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_3$ is $CH_3$, $Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_3$ is $CH_3$,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_3$ is $CH_3$,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_3$ is $CH_3$,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_3$ is $CH_3$,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_3$ is $CH_3$,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_3$ is $CH_3$, $Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_3$ is $CH_3$,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_3$ is $CH_3$,
$Z_1$ is $CF_3$, $Z_2$ is, and —S—CH$_2$CF$_3$, —SO—CH$_2$CF$_3$, —SO$_2$—CH$_2$CF$_3$
$Z_3$ is CH$_3$.
In another preferred embodiment $R_3$ is CH$_3$ and $R_2$ is H.
In another preferred embodiment, $R_3$ is CH$_3$ and $R_2$ is H and $R_1$ is H or CH$_3$.
In another preferred embodiment, $R_3$ is CH$_3$ and $R_2$ is H and $R_1$ is H.
In another preferred embodiment
$A_1$ is CH,
$R_1$ is H,
$R_2$ is H,
$R_3$ is CH$_3$,
$Z_1$ is CF$_3$ or C$_2$F$_5$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_1$ is H,
$R_2$ is H,
$R_3$ is CH$_3$,
$Z_1$ is CF$_3$ or C$_2$F$_5$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_1$ is H,
$R_2$ is H,
$R_3$ is CH$_3$,
$Z_1$ is CF$_3$ or C$_2$F$_5$,
$Z_2$ is —S—CH$_3$—S—C$_2$H$_5$, —SO—CH$_3$, —SO$_2$—CH$_3$, and
$Z_3$ is CH$_3$.
In another preferred embodiment
$R_1$ is H,
$R_2$ is H,
$R_3$ is CH$_3$,
$Z_1$ is CF$_3$ or C$_2$F$_5$,
$Z_2$ is —S—CH$_3$, —SO—CH$_3$, —SO$_2$—CH$_3$, and
$Z_3$ is CH$_3$.
In another preferred embodiment
$A_1$ is CH,
$R_1$ is H,
$R_2$ is H,
$R_3$ is CH$_3$,
$Z_1$ is CF$_3$ or C$_2$F$_5$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.
In another preferred embodiment
$A_1$ is CH,
$R_1$ is H,
$R_2$ is H,
$R_3$ is CH$_3$,
$Z_1$ is CF$_3$ or C$_2$F$_5$,
$Z_2$ is, and —S—CH$_2$CF$_3$, —SO—CH$_2$CF$_3$, —SO$_2$—CH$_2$CF$_3$
$Z_3$ is CH$_3$.
In another preferred embodiment
$A_1$ is CH,
$R_1$ is H,
$R_2$ is H,
$R_3$ is CH$_3$,
$Z_1$ is C$_2$F,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_1$ is H,
$R_2$ is H,
$R_3$ is CH$_3$,
$Z_1$ is C$_2$F$_5$,
$Z_2$ is —S—CH$_3$, —SO—CH$_3$, —SO$_2$—CH$_3$, —S—C$_2$H$_5$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_1$ is H,
$R_2$ is H,
$R_3$ is CH$_3$,
$Z_1$ is C$_2$F$_5$,
$Z_2$ is —S—CH$_3$—S—C$_2$H$_5$, —SO—CH$_3$, —SO$_2$—CH$_3$, and
$Z_3$ is CH$_3$.
In another preferred embodiment
$A_1$ is CH,
$R_1$ is H,
$R_2$ is H,
$R_3$ is CH$_3$,
$Z_1$ is C$_2$F$_5$,
$Z_2$ is —S—CH$_3$, —SO—CH$_3$, —SO$_2$—CH$_3$, and
$Z_3$ is CH$_3$.
In another preferred embodiment
$A_1$ is CH,
$R_1$ is H,
$R_2$ is H,
$R_3$ is CH$_3$,
$Z_1$ is C$_2$F$_5$,
$Z_2$ is, and —S—CF$_3$, —SO—CF$_3$, —SO$_2$—CF$_3$, —S—CH$_2$CF$_3$, —SO—CH$_2$CF$_3$, —SO$_2$—CH$_2$CF$_3$
$Z_3$ is CH$_3$.
In another preferred embodiment
$A_1$ is CH,
$R_1$ is H,
$R_2$ is H,
$R_3$ is CH$_3$,
$Z_1$ is C$_2$F$_5$,
$Z_2$ is, and —S—CH$_2$CF$_3$, —SO—CH$_2$CF$_3$, —SO$_2$—CH$_2$CF$_3$
$Z_3$ is CH$_3$.
In another preferred embodiment
$A_1$ is CH,
$R_1$ is H,
$R_2$ is H,
$R_3$ is CH$_3$,
$Z_1$ is CF$_3$,
$Z_2$ is —S—CH$_3$, —SO—CH$_3$, —SO$_2$—CH$_3$, —S—C$_2$H$_5$, —SO—C$_2$H$_5$, —SO$_2$—C$_2$H$_5$, —S—CF$_3$, —SO—CF$_3$, —SO$_2$—CF$_3$, —S—CH$_2$—CF$_3$, —SO—CH$_2$—CF$_3$, or —SO$_2$—CH$_2$—CF$_3$, and
$Z_3$ is CH$_3$.
In another preferred embodiment
$A_1$ is CH,
$R_1$ is H,
$R_2$ is H, $R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is H,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_2$ is H,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_2$ is H,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is H,
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment $R_3$ is $CH_3$ and $R_2$ is H and $R_1$ is $CH_3$.
In another preferred embodiment
$A_1$ is CH,
$R_1$ is $CH_3$,
$R_2$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$R_1$ is $CH_3$,
$R_2$ is H,
$R_3$ is $CH_3$,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is $CH_3$,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is H,
$R_3$ is $CH_3$,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is H,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is H,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is H,
$R_3$ is $CH_3$,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is $CH_3$,
$Z_1$ is $C_2F_5$, $Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is H,
$R_3$ is $CH_3$,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is H,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is H,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is H,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_2$ is H,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is CH,
$R_1$ is $CH_3$,
$R_2$ is H,
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment $R_3$ is $CH_3$ and $R_2$ is H and $A_1$ is N.
In another preferred embodiment
$A_1$ is N,
$R_1$ is H,
$R_2$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_2$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_2$ is H,
$R_3$ is $CH_3$,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is H,
$R_2$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is H,
$R_2$ is H,
$R_3$ is $CH_3$,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is H,
$R_2$ is H,
$R_3$ is $CH_3$,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is H,
$R_2$ is H,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is H,
$R_2$ is H,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is H,
$R_2$ is H,
$R_3$ is $CH_3$,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.

In another preferred embodiment
$A_1$ is N,
$R_1$ is H,
$R_2$ is H,
$R_3$ is $CH_3$,
$Z_1$ is $C_2F_5$,
$Z_2$ is —S—$CH_3$, —SO—$CH_3$, —$SO_2$—$CH_3$, and
$Z_3$ is $CH_3$.

In another preferred embodiment
$A_1$ is N,
$R_1$ is H,
$R_2$ is H,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is H,
$R_2$ is H,
$R_3$ is $CH_3$,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is H,
$R_2$ is H,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is H,
$R_2$ is H,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is H,
$R_2$ is H,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.

In another preferred embodiment
$A_1$ is N,
$R_1$ is H,
$R_2$ is H,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.

In another preferred embodiment
$A_1$ is N,
$R_1$ is H,
$R_2$ is H,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is H,
$R_2$ is H,
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is $CH_3$,
$R_2$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is $CH_3$,
$R_2$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is $CH_3$,
$R_2$ is H,
$R_3$ is $CH_3$,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_2$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_2$ is H,
$R_3$ is $CH_3$,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is H,
$R_3$ is $CH_3$,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is H,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is H,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is H,
$R_3$ is $CH_3$,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_2$ is H,
$R_3$ is $CH_3$,
$Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_2$ is H,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is H,
$R_3$ is $CH_3$,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is H,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is H,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is H,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_2$ is H,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_2$ is H,
$R_3$ is $CH_3$, $Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is H,
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment $R_3$ is $CH_3$ and $R_2$ is CN.
In another preferred embodiment, $R_3$ is $CH_3$ and $R_2$ is CN and $R_1$ is H or $CH_3$.
In another preferred embodiment, $R_3$ is $CH_3$ and $R_2$ is CN and $R_1$ is H.
In another preferred embodiment
$A_1$ is CH,
$R_1$ is H,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is CN,
$R_3$ is $CH_3$,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$R_1$ is H,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_2$ is CN,
$R_3$ is $CH_3$,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is CN,
$R_3$ is $CH_3$,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is CN,
$R_3$ is $CH_3$,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_2$ is CN,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is CN,
$R_3$ is $CH_3$,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is CN,
$R_3$ is $CH_3$, $Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is CN,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is H,
$R_2$ is CN,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is H,
$R_2$ is CN,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is H,
$R_2$ is CN,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is H,
$R_2$ is CN,
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment $R_3$ is $CH_3$ and $R_2$ is CN and $R_1$ is $CH_3$.
In another preferred embodiment
$A_1$ is CH,
$R_1$ is $CH_3$,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$R_1$ is $CH_3$,
$R_2$ is CN,
$R_3$ is $CH_3$,
$Z_1$ is $CF_3$ or $C_2F$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_2$ is CN,
$R_3$ is $CH_3$,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is CN,
$R_3$ is $CH_3$,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is CN,
$R_3$ is $CH_3$, $Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_2$ is CN,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is CN,
$R_3$ is $CH_3$,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is CN,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is CN,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is CH,
$R_1$ is $CH_3$,
$R_2$ is CN,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is CH,
$R_1$ is $CH_3$,
$R_2$ is CN,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is CH,
$R_1$ is $CH_3$,
$R_2$ is CN,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is CH,
$R_1$ is $CH_3$,
$R_2$ is CN,
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment $R_2$ is CN and $A_1$ is N.
In another preferred embodiment
$A_1$ is N,
$R_1$ is H,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is H,
$R_2$ is CN,
$R_3$ is $CH_3$,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is H,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is H,
$R_2$ is CN,
$R_3$ is $CH_3$,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is H,
$R_2$ is CN,
$R_3$ is $CH_3$,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is H,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is H,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is H,
$R_2$ is CN,
$R_3$ is $CH_3$,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.

In another preferred embodiment
$A_1$ is N,
$R_1$ is H,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, and
$Z_3$ is $CH_3$.

In another preferred embodiment
$A_1$ is N,
$R_1$ is H,
$R_2$ is CN,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is H,
$R_2$ is CN,
$R_3$ is $CH_3$,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is H,
$R_2$ is CN,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is H,
$R_2$ is CN,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is H,
$R_2$ is CN,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.

In another preferred embodiment
$A_1$ is N,
$R_1$ is H,
$R_2$ is CN,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.

In another preferred embodiment
$A_1$ is N,
$R_1$ is H,
$R_2$ is CN,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is H,
$R_2$ is CN,
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.

In another preferred embodiment
$A_1$ is N,
$R_1$ is $CH_3$,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is $CH_3$,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is CN,
$R_3$ is $CH_3$,
$Z_1$ is $CF_3$ or $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_2$ is CN,
$R_3$ is $CH_3$,
$Z_1$ is $CF_3$ or $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_2$ is CN,
$R_3$ is $CH_3$,
$Z_1$ is $CF_3$ or $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is CN,
$R_3$ is $CH_3$,
$Z_1$ is $CF_3$ or $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.

In another preferred embodiment
$A_1$ is N,
$R_1$ is $CH_3$,
$R_2$ is CN,
$R_3$ is $CH_3$,
$Z_1$ is $C_2F_5$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$,
$R_2$ is CN,
$R_3$ is $CH_3$,
$Z_1$ is $C_2F_5$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_2$ is CN,
$R_3$ is $CH_3$,
$Z_1$ is $C_2F_5$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is CN,
$R_3$ is $CH_3$,
$Z_1$ is $C_2F_5$,
$Z_2$ is, and —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is CN,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —SO—$C_2H_5$, —$SO_2$—$C_2H_5$, —S—$CF_3$, —SO—$CF_3$, —$SO_2$—$CF_3$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is CN,
$R_3$ is $CH_3$,
$Z_1$ is $CF_3$,
$Z_2$ is —S—$CH_3$, —SO—$CH_3$, —$SO_2$—$CH_3$, —S—$C_2H_5$, —S—$CH_2$—$CF_3$, —SO—$CH_2$—$CF_3$, or —$SO_2$—$CH_2$—$CF_3$, and
$Z_3$ is $CH_3$.
In another preferred embodiment
$A_1$ is N,
$R_1$ is $CH_3$,
$R_2$ is CN,
$R_3$ is $CH_3$,
$Z_1$ is $CF_3$,
$Z_2$ is —S—$CH_3$—S—$C_2H_5$, —SO—$CH_3$, —$SO_2$—$CH_3$, and
$Z_3$ is $CH_3$.
In another preferred embodiment
$A_1$ is N,
$R_1$ is $CH_3$, $R_2$ is CN,
$R_3$ is $CH_3$,
$Z_1$ is $CF_3$,
$Z_2$ is —S—$CH_3$, —SO—$CH_3$, —$SO_2$—$CH_3$, and
$Z_3$ is $CH_3$.
In another preferred embodiment
$A_1$ is N,
$R_1$ is $CH_3$,
$R_2$ is CN,
$R_3$ is $CH_3$,
$Z_1$ is $CF_3$,
$Z_2$ is, and —S—$CF_3$, —SO—$CF_3$, —$SO_2$—$CF_3$, —S—$CH_2CF_3$, —SO—$CH_2CF_3$, —$SO_2$—$CH_2CF_3$
$Z_3$ is $CH_3$.
In another preferred embodiment
$A_1$ is N,
$R_1$ is $CH_3$,
$R_2$ is CN,
$R_3$ is $CH_3$,
$Z_1$ is $CF_3$,
$Z_2$ is, and —S—$CH_2CF_3$, —SO—$CH_2CF_3$, —$SO_2$—$CH_2CF_3$
$Z_3$ is $CH_3$.
In another preferred embodiment, compounds of formula (I)

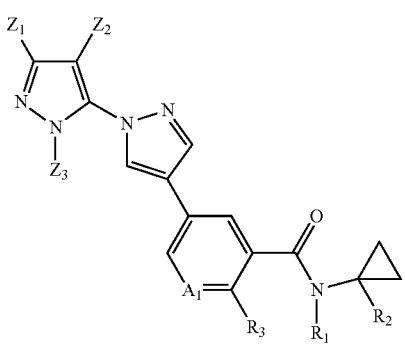

are compounds wherein
$A_1$ is N or CH,
$R_1$ is H,
$R_2$ is CN or H,
$R_3$ is $C_1$-$C_4$-alkyl, preferably methyl, or an halogen selected from the group consisting of I, Br, F, Cl, preferably Cl,
$Z_1$ is perfluorinated $C_1$-$C_4$-alkyl, preferably $CF_3$ or $CH_2CF_3$,
$Z_2$ is, and —S—$C_1$-$C_4$-alkyl —SO—$C_1$-$C_4$-alkyl or $SO_2$—$C_1$-$C_4$-alkyl, preferably —S—$CH_3$, —SO—$CH_3$, —$SO_2$—$CH_3$, —S—$CH_2$—$CH_3$, —SO—$CH_2$—$CH_3$, —$SO_2$—$CH_2$—$CH_3$, —S—$CH(CH_3)_2$, —SO—$CH(CH_3)_2$, —$SO_2$—$CH(CH_3)_2$, more preferably —S—$CH_3$, —SO—$CH_3$, —$SO_2$—$CH_3$, —S—$CH_2$—$CH_3$, —SO—$CH_2$—$CH_3$, —S—$CH(CH_3)_2$,
$Z_3$ is $CH_3$.

The compounds according to the invention can be prepared by customary methods known to those skilled in the art.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixture of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded herefrom are methods for the surgical or therapeutic treatment of the human or animal body and diagnostic methods carried out on the human or animal body.

The invention furthermore relates to the use of the compounds of the formula (I) as pesticides, in particular crop protection agents.

In the context of the present application, the term "pesticide" in each case also always comprises the term "crop protection agent".

The compounds of the formula (I), having good plant tolerance, favourable homeotherm toxicity and good environmental compatibility, are suitable for protecting plants and plant organs against biotic and abiotic stressors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are active against normally sensitive and resistant species and against all or some stages of development. The abovementioned pests include:

pests from the phylum of the Arthropoda, in particular from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus (=Polyphagotarsonemus latus), Hyalomma* spp., *Ixodes* spp., *Latrodectus* spp., *Loxosceles* spp., *Neutrombicula autumnalis, Nuphersa* spp., *Oligonychus* spp., for example *Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri (=Metatetranychus citri), Panonychus ulmi (=Metatetranychus ulmi), Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici*;

from the class of the Chilopoda, for example *Geophilus* spp., *Scutigera* spp.;
from the order or the class of the Collembola, for example *Onychiurus armatus; Sminthurus viridis;*
from the class of the Diplopoda, for example *Blaniulus guttulatus;*
from the class of the Insecta, for example from the order of the Blattodea, for example *Blatta orientalis, Blattella asahinai, Blattella germanica, Leucophaea maderae, Panchlora* spp., *Parcoblatta* spp., *Periplaneta* spp., for example *Periplaneta americana, Periplaneta australasiae, Supella longipalpa;* from the order of the Coleoptera, for example *Acalymma vittatum, Acanthoscelides obtectus, Adoretus* spp., *Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;*
from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex;*
from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Carneocephala fulgida,*

*Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Nephotettix* spp., for example *Nephotettix cincticeps, Nephotettix nigropictus, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurygaster* spp., *Halyomorpha halys, Heliopeltis* spp., *Horcias nobilellus, Leptocorisa* spp., *Leptocorisa varicomis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Monalonion atratum, Nezara* spp., for example *Nezara viridula, Oebalus* spp., *Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Diprion* spp., for example *Diprion similis, Hoplocampa* spp., for example *Hoplocampa cookei, Hoplocampa testudinea, Lasius* spp., *Linepithema humile, Monomorium pharaonis, Sirex* spp., *Solenopsis invicta, Tapinoma* spp., *Urocerus* spp., *Vespa* spp., for example *Vespa crabro, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Microtermes obesi, Odontotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Etiella* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Gracillaria* spp., *Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens Hofmannophila pseudospretella, Homoeosoma* spp., *Homona* spp., *Hyponomeuta padella, Kakivoria flavofasciata, Laphygma* spp., *Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema mel-* anopus, *Oulema oryzae*, *Panolis flammea*, *Parnara* spp., *Pectinophora* spp., for example *Pectinophora gossypiella*, *Perileucoptera* spp., *Phthorimaea* spp., for example *Phthorimaea operculella*, *Phyllocnistis citrella*, *Phyllonorycter* spp., for example *Phyllonorycter blancardella*, *Phyllonorycter crataegella*, *Pieris* spp., for example *Pieris rapae*, *Platynota stultana*, *Plodia interpunctella*, *Plusia* spp., *Plutella xylostella* (=*Plutella maculipennis*), *Prays* spp., *Prodenia* spp., *Protoparce* spp., *Pseudaletia* spp., for example *Pseudaletia unipuncta*, *Pseudoplusia includens*, *Pyrausta nubilalis*, *Rachiplusia nu*, *Schoenobius* spp., for example *Schoenobius bipunctifer*, *Scirpophaga* spp., for example *Scirpophaga innotata*, *Scotia segetum*, *Sesamia* spp., for example *Sesamia inferens*, *Sparganothis* spp., *Spodoptera* spp., for example *Spodoptera eradiana*, *Spodoptera exigua*, *Spodoptera frugiperda*, *Spodoptera praefica*, *Stathmopoda* spp., *Stomopteryx subsecivella*, *Synanthedon* spp., *Tecia solanivora*, *Thermesia gemmatalis*, *Tinea cloacella*, *Tinea pellionella*, *Tineola bisselliella*, *Tortrix* spp., *Trichophaga tapetzella*, *Trichoplusia* spp., for example *Trichoplusia ni*, *Tryporyza incertulas*, *Tuta absoluta*, *Virachola* spp.;

from the order of the Orthoptera or Saltatoria, for example *Acheta domesticus*, *Dichroplus* spp., *Gryllotalpa* spp., for example *Gryllotalpa gryllotalpa*, *Hieroglyphus* spp., *Locusta* spp., for example *Locusta migratoria*, *Melanoplus* spp., for example *Melanoplus devastator*, *Paratlanticus ussuriensis*, *Schistocerca gregaria*;

from the order of the Phthiraptera, for example *Damalinia* spp., *Haematopinus* spp., *Linognathus* spp., *Pediculus* spp., *Phylloxera vastatrix*, *Phthirus pubis*, *Trichodectes* spp.;

from the order of the Psocoptera, for example *Lepinotus* spp., *Liposcelis* spp.; from the order of the Siphonaptera, for example, *Ceratophyllus* spp., *Ctenocephalides* spp., for example *Ctenocephalides canis*, *Ctenocephalides felis*, *Pulex irritans*, *Tunga penetrans*, *Xenopsylla cheopis*;

from the order of the Thysanoptera, for example *Anaphothrips obscurus*, *Baliothrips biformis*, *Drepanothrips reuteri*, *Enneothrips flavens*, *Frankliniella* spp., for example *Frankliniella fusca*, *Frankliniella occidentalis*, *Frankliniella schultzei*, *Frankliniella tritici*, *Frankliniella vaccinii*, *Frankliniella williamsi*, *Heliothrips* spp., *Hercinothrips femoralis*, *Rhipiphorothrips cruentatus*, *Scirtothrips* spp., *Taeniothrips cardamomi*, *Thrips* spp., for example *Thrips palmi*, *Thrips tabaci*;

from the order of the Zygentoma (=*Thysanura*), for example *Ctenolepisma* spp., *Lepisma saccharina*, *Lepismodes inquilinus*, *Thermobia domestica*;

from the class of the Symphyla, for example *Scutigerella* spp., for example *Scutigerella immaculata*;

pests from the phylum of the Mollusca, for example from the class of the Bivalvia, for example *Dreissena* spp., and also from the class of the Gastropoda, for example *Arion* spp., for example *Arion ater rufus*, *Biomphalaria* spp., *Bulinus* spp., *Deroceras* spp., for example *Deroceras laeve*, *Galba* spp., *Lymnaea* spp., *Oncomelania* spp., *Pomacea* spp., *Succinea* spp.;

animal and human parasites from the phyla of the Platylminthes and Nematoda, for example *Aelurostrongylus* spp., *Amidostomum* spp., *Ancylostoma* spp, *Angiostrongylus* spp., *Anisakis* spp., *Anoplocephala* spp., *Ascaris* spp., *Ascaridia* spp., *Baylisascaris* spp., *Brugia* spp., *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp, *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp., *Toxocara* spp., *Trichinella* spp., *Trichobilharzia* spp., *Trichostrongylus* spp., *Trichuris* spp., *Uncinaria* spp., *Wuchereria* spp.;

plant pests from the phylum of the Nematoda, i.e. phytoparasitic nematodes, in particular *Aglenchus* spp., for example *Aglenchus agricola*, *Anguina* spp., for example *Anguina tritici*, *Aphelenchoides* spp., for example *Aphelenchoides arachidis*, *Aphelenchoides fragariae*, *Belonolaimus* spp., for example *Belonolaimus gracilis*, *Belonolaimus longicaudatus*, *Belonolaimus nortoni*, *Bursaphelenchus* spp., for example *Bursaphelenchus cocophilus*, *Bursaphelenchus eremus*, *Bursaphelenchus xylophilus*, *Cacopaurus* spp., for example *Cacopaurus pestis*, *Criconemella* spp., for example *Criconemella curvata*, *Criconemella onoensis*, *Criconemella ornata*, *Criconemella rusium*, *Criconemella xenoplax* (=*Mesocriconema xenoplax*), *Criconemoides* spp., for example *Criconemoides ferniae*, *Criconemoides onoense*, *Criconemoides ornatum*, *Ditylenchus* spp., for example *Ditylenchus dipsaci*, *Dolichodorus* spp., *Globodera* spp., for example *Globodera pallida*, *Globodera rostochiensis*, *Helicotylenchus* spp., for example *Helicotylenchus dihystera*, *Hemicriconemoides* spp., *Hemicycliophora* spp., *Heterodera* spp., for example *Heterodera avenae*, *Heterodera glycines*, *Heterodera schachtii*, *Hoplolaimus* spp., *Longidorus* spp., for example *Longidorus africanus*, *Meloidogyne* spp., for example *Meloidogyne chitwoodi*, *Meloidogyne fallax*, *Meloidogyne hapla*, *Meloidogyne incognita*, *Meloinema* spp., *Nacobbus* spp., *Neotylenchus* spp., *Paraphelenchus* spp., *Paratrichodorus* spp., for example *Paratrichodorus minor*, *Pratylenchus* spp., for example *Pratylenchus penetrans*, *Pseudohalenchus* spp., *Psilenchus* spp., *Punctodera* spp., *Quinisulcius* spp., *Radopholus* spp., for example *Radopholus citrophilus*, *Radopholus similis*, *Rotylenchulus* spp., *Rotylenchus* spp., *Scutellonema* spp., *Subanguina* spp., *Trichodorus* spp., for example *Trichodorus obtusus*, *Trichodorus primitivus*, *Tylenchorhynchus* spp., for example *Tylenchorhynchus annulatus*, *Tylenchulus* spp., for example *Tylenchulus semipenetrans*, *Xiphinema* spp., for example *Xiphinema index*.

Furthermore, it is possible to control, from the subkingdom of the Protozoa, the order of the Coccidia, for example *Eimeria* spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, viricides (including agents against viroids) or as agents against MLO (*mycoplasma*-like organisms) and RLO (*rickettsia*-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are prepared either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam-formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

It is possible to use colorants such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc as further auxiliaries in the formulations and the use forms derived therefrom.

Additional components may be stabilizers, such as low-temperature stabilizers, preservatives, antioxidants, light stabilizers or other agents which improve chemical and/or physical stability. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and thereby increase the mobility of active compounds in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001 and 98% by weight of the compound of the formula (I) or, with particular preference, between 0.01% and 95% by weight of the compound of the formula (I), more preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms is usually between 0.00000001 and 95% by weight of the compound of the formula (I), preferably between 0.00001 and 1% by weight, based on the weight of the use form.

The compounds are employed in a customary manner appropriate for the use forms.

Mixtures

The compounds of the formula (I) may also be employed as a mixture with one or more suitable fungicides, bactericides, acaricides, molluscicides, nematicides, insecticides, microbiologicals, beneficial species, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, such active compound combinations may improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

Furthermore, the compounds of the formula (I) can be present in a mixture with other active compounds or semiochemicals such as attractants and/or bird repellants and/or plant activators and/or growth regulators and/or fertilizers. Likewise, the compounds of the formula (I) can be used to improve plant properties such as, for example, growth, yield and quality of the harvested material.

In a particular embodiment according to the invention, the compounds of the formula (I) are present in formulations or the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active compounds identified here by their common names are known and are described, for example, in the pesticide handbook ("The Pesticide Manual" 16th Ed., British Crop Protection Council 2012) or can be found on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, such as, for example, cyclodiene-organochlorines, for example chlordane and endosulfan or phenylpyrazoles (fiproles), for example ethiprole and fipronil.

(3) Sodium channel modulators/voltage-gated sodium channel blockers such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinergic acetylcholine receptor (nAChR) agonists, such as, for example, neonicotinoids, e.g. acetamiprid, clothianidin, dinotefuran, imidacloprid, nitenpyram, thiacloprid and thiamethoxam or nicotine or sulfoxaflor.

(5) Allosteric activators of the nicotinergic acetylcholine receptor (nAChR) such as, for example, spinosyns, e.g. spinetoram and spinosad.

(6) Chloride channel activators, such as, for example, avermectins/milbemycins, for example abamectin, emamectin benzoate, lepimectin and milbemectin.

(7) Juvenile hormone imitators such as, for example, juvenile hormone analogues, e.g. hydroprene, kinoprene and methoprene or fenoxycarb or pyriproxyfen.

(8) Active compounds with unknown or nonspecific mechanisms of action such as, for example, alkyl halides, e.g. methyl bromide and other alkyl halides; or chloropicrine or sulphuryl fluoride or borax or tartar emetic.

(9) Selective antifeedants, for example pymetrozine or flonicamid.

(10) Mite growth inhibitors, for example clofentezine, hexythiazox and diflovidazin or etoxazole.

(11) Microbial disruptors of the insect gut membrane, for example Bacillus thuringiensis subspecies israelensis, Bacillus sphaericus, Bacillus thuringiensis subspecies aizawai, Bacillus thuringiensis subspecies kurstaki, Bacillus thuringiensis subspecies tenebrionis, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors such as, for example, diafenthiuron or organotin compounds, for example azocyclotin, cyhexatin and fenbutatin oxide or propargite or tetradifon;

(13) Oxidative phosphorylation decouplers acting by interrupting the H proton gradient such as, for example, chlorfenapyr, DNOC and sulfluramid.

(14) Nicotinergic acetylcholine receptor antagonists such as, for example, bensultap, cartap hydrochloride, thiocylam, and thiosultap-sodium.

(15) Chitin biosynthesis inhibitors, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (in particular for Diptera, i.e. dipterans) such as, for example, cyromazine.

(18) Ecdysone receptor agonists such as, for example, chromafenozide, halofenozide, methoxyfenozide and tebufenozide.

(19) Octopaminergic agonists such as, for example, amitraz.

(20) Complex-III electron transport inhibitors such as, for example, hydramethylnone or acequinocyl or fluacrypyrim.

(21) Complex-I electron transport inhibitors, for example from the group of the METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase such as, for example, tetronic and tetramic acid derivatives, e.g. spirodiclofen, spiromesifen and spirotetramat.

(24) Complex-IV electron transport inhibitors such as, for example, phosphines, e.g. aluminium phosphide, calcium phosphide, phosphine and zinc phosphide or cyanide.

(25) Complex II electron transport inhibitors, such as, for example, cyenopyrafen and cyflumetofen.

(28) Ryanodine receptor effectors, such as, for example, diamides, e.g. chlorantraniliprole, cyantraniliprole and flubendiamide, further active compounds such as, for example, afidopyropen, azadirachtin, benclothiaz, benzoximate, bifenazate, bromopropylate, chinomethionat, cryolite, dicofol, diflovidazin, fluensulfone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; furthermore preparations based on Bacillus firmus (I-1582, BioNeem, Votivo), and also the following compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) and 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494), 3-(2,5-dimethylphenyl)-4-hydroxy-8-methoxy-1,8-diazaspiro[4.5] dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl] carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl) sulphonyl]-6-(trifluoromethyl)imidazo[1,2-a]pyridine-2-carboxamide (known from WO2010/129500), 4-[5-(3,5- dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N'-nitro-2-pentylidenehydrazinecarboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Fungicides

The active compounds specified herein by their common name are known and described, for example, in "Pesticide Manual" or on the Internet (for example: http://www.alanwood.net/pesticides).

(1) Inhibitors of ergosterol biosynthesis such as, for example, (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difuoromethyl)-2-methyl-4-[3-(trimethylsily)propoxy]phenyl}-N-ethyl-N-methylimidoformamide, (1.63)N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors) such as, for example, (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-empimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid (3) Respiration inhibitors (respiratory chain inhibitors) acting on complex III of the respiratory chain such as, for example, (3.1) ametoctradin, (3.2) amisulbrom, (3.3) azoxystrobin, (3.4) cyazofamid, (3.5) coumethoxystrobin, (3.6) coumoxystrobin, (3.5) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenyl)ethanamide, (3.25) (2E)-2-(methoxyimino)-N-methyl-2-{2-[(E)-({1-[3-(trifluoromethyl)phenyl]ethoxy}imino)methyl]phenyl}ethanamide, (3.26) (2E)-2-{2-[({[(1E)-1-(3-{[(E)-1-fluoro-2-phenylethenyl]oxy}phenyl)ethylidene]amino)oxy]methyl]phenyl}-2-(methoxyimino)-N-methylethanamide, (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-

[({cyclopropyl[(4-methoxyphenyl)imino]methyl}sulphanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide, (4) inhibitors of mitosis and cell division such as, for example, (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine and (4.14) 3-chloro-5-(6-chloropyridin-3-yl)-6-methyl-4-(2,4,6-trifluorophenyl)pyridazine.

(5) Compounds having multisite activity such as, for example, (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxychloride, (5.9) copper sulphate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copperoxine, (5.28) propamidine, (5.29) propineb, (5.30) sulphur and sulphur preparations such as, for example calcium polysulphide, (5.31) thiram, (5.32) tolylfluanid, (5.33) zineb, (5.34) ziram and (5.35) anilazine.

(6) Resistance inducers such as, for example, (6.1) acibenzolar-S-methyl, (6.2) isotianil, (6.3) probenazole, (6.4) tiadinil and (6.5) laminarin.

(7) Inhibitors of amino acid and protein biosynthesis such as, for example, (7.1), (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors such as, for example, (8.1) fentin acetate, (8.2) fentin chloride, (8.3) fentin hydroxide and (8.4) silthiofam.

(9) Inhibitors of cell wall synthesis such as, for example, (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Inhibitors of lipid and membrane synthesis such as, for example, (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4) fthalide, (11.5) pyroquilon, (11.6) tricyclazole and (11.7) 2,2,2-trifluoroethyl {3-methyl-1-[(4-methylbenzoyl)amino]butan-2-yl}carbamate.

(12) Inhibitors of nucleic acid synthesis such as, for example, (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors such as, for example, (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers such as, for example, (14.1) binapacryl, (14.2) dinocap, (14.3) ferimzone, (14.4) fluazinam and (14.5) meptyldinocap.

(15) Further compounds such as, for example, (15.1) benthiazole, (15.2) bethoxazine, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat methylsulphate, (15.17) diphenylamine, (15.18) EcoMate, (15.19) fenpyrazamine, (15.20) flumetover, (15.21) fluorimid, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulphonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7 (2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulphonohydrazide, (15.74) 5-fluoro-2-[(4-fluorobenzyl)oxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl (2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91) phenazine-1-carboxylic acid, (15.92) quinolin-8-ol, (15.93) quinolin-8-ol sulphate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl]nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulphonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulfanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulphanyl)-1-{[rel(2R,3S)-3-(2-chlorophenyl)-2-(2,4-difluorophenyl)oxiran-2-yl]methyl}-1H-1,2,4-triazole, (15.136) 5-(allylsulphanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazol-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazole-5-amine. All mixing components mentioned in classes (1) to (15) can, if they are capable on the basis of their functional groups, optionally form salts with suitable bases or acids.

Biological Pesticides as Mixing Components

The compounds of the formula (I) can be combined with biological pesticides.

Biological pesticides comprise in particular bacteria, fungi, yeasts, plant extracts and products formed by microorganisms, including proteins and secondary metabolites.

Biological pesticides comprise bacteria such as spore-forming bacteria, root-colonising bacteria and bacteria which act as biological insecticides, fungicides or nematicides.

Examples of such bacteria which are employed or can be used as biological pesticides are:

*Bacillus amyloliquefaciens*, strain FZB42 (DSM 231179), or *Bacillus cereus*, in particular *B. cereus* strain CNCM I-1562 or *Bacillus firmus*, strain I-1582 (Accession number CNCM I-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, in particular *B. thuringiensis* subspecies *israelensis* (serotype H-14), strain AM65-52 (Accession No. ATCC 1276), or *B. thuringiensis* subsp. *aizawai*, in particular strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are employed or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (now: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39. (Accession Number CNCM I-952).

Examples of viruses which are employed or can be used as biological pesticides are:

*Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are: *Agrobacterium* spp., *Azorhizobium caulinodans*, *Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., in particular *Rhizobium trifolii*, *Rhizopogon* spp., *Scleroderma* spp., *Suillus* spp., *Streptomyces* spp.

Examples of plant extracts and products formed by microorganisms including proteins and secondary metabolites which are employed or can be used as biological pesticides are:
*Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), *Pyrethrum/Pyrethrins*, *Quassia amara*, *Quercus*, *Quillaja*, *Regalia*, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, *Veratrin*, *Viscum album*, *Brassicaceae* extract, in particular oilseed rape powder or mustard powder.

Safener as Mixing Components

The compounds of the formula (I) can be combined with safeners such as, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Here, plants are to be understood to mean all plants and plant parts such as wanted and unwanted wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapevines). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts should be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested plants and vegetative and generative propagation material, for example seedlings, tubers, rhizomes, cuttings and seeds.

Treatment according to the invention of the plants and plant parts with the compounds of the formula (I) is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. The invention is used with particular preference to treat plants of the respective commercially customary cultivars or those that are in use. Plant cultivars are to be understood as meaning plants having new properties ("traits") and which have been obtained by conventional breeding, by mutagenesis or by recombinant DNA techniques. They can be cultivars, varieties, bio- or genotypes.

Transgenic Plant, Seed Treatment and Integration Events

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products. Further and particularly emphasized examples of such properties are increased resistance of the plants against animal and microbial pests, such as against insects, arachnids, nematodes, mites, slugs and snails owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIB2, Cry9c Cry2Ab, Cry3Bb and CryIF and also combinations thereof), furthermore increased resistance of the plants against phytopathogenic fungi, bacteria and/or viruses owing, for example, to systemic acquired resistance (SAR), systemin, phytoalexins, elicitors and also resistance genes and correspondingly expressed proteins and toxins, and also increased tolerance of the plants to certain herbicidally active compounds, for example imidazolinones, sulphonylureas, glyphosate or phosphinothricin (for example the "PAT" gene). The genes which impart the desired traits in question may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails.

Crop Protection—Types of Treatment

The treatment of the plants and plant parts with the compounds of the formula (I) is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for liquid seed treatment, a water-soluble powder for slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. the compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This may be done, for example, by drenching, or by mixing into the soil or the nutrient solution, i.e. the locus of the plant (e.g. soil or hydroponic systems) is impregnated with a liquid form of the compounds of the formula (I), or by soil application, i.e. the compounds of the formula (I) according to the invention are introduced in solid form (e.g. in the form of granules) into the locus of the plants. In the case of paddy rice crops, this can also be done by metering the compound of the formula (I) in a solid application form (for example as granules) into a flooded paddy field.

Treatment of Seed

The control of animal pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is furthermore desirable to optimize the amount of active compound employed in such a way as to provide optimum protection for the seed and the germinating plant from attack by animal pests, but without damaging the plant itself by the active compound employed. In particular, methods for the treatment of seed should also take into consideration the intrinsic insecticidal or nematicidal properties of pest-resistant or -tolerant transgenic plants in order to achieve optimum protection of the seed and also the germinating plant with a minimum of pesticides being employed.

The present invention therefore in particular also relates to a method for the protection of seed and germinating plants, from attack by pests, by treating the seed with one of the compounds of the formula (I). The method according to the invention for protecting seed and germinating plants against attack by pests furthermore comprises a method where the seed is treated simultaneously in one operation or sequentially with a compound of the formula (I) and a mixing component. It also comprises a method where the seed is treated at different times with a compound of the formula (I) and a mixing component.

The invention likewise relates to the use of the compounds of the formula (I) for the treatment of seed for protecting the seed and the resulting plant from animal pests.

Furthermore, the invention relates to seed which has been treated with a compound of the formula (I) according to the invention so as to afford protection from animal pests. The invention also relates to seed which has been treated simultaneously with a compound of the formula (I) and a mixing component. The invention furthermore relates to seed which has been treated at different times with a compound of the formula (I) and a mixing component. In the case of seed which has been treated at different points in time with a compound of the formula (I) and a mixing component, the individual substances may be present on the seed in different layers. Here, the layers comprising a compound of the formula (I) and mixing components may optionally be separated by an intermediate layer. The invention also relates to seed where a compound of the formula (I) and a mixing component have been applied as component of a coating or as a further layer or further layers in addition to a coating.

Furthermore, the invention relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this manner, the immediate treatment of the crop at the time of sowing or shortly thereafter can be dispensed with.

It has to be considered a further advantage that by treatment of the seed with a compound of the formula (I), germination and emergence of the treated seed may be enhanced.

It is likewise to be considered advantageous that compounds of the formula (I) can be used in particular also for transgenic seed.

Furthermore, compounds of the formula (I) can be employed in combination with compositions or compounds of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. In particular, this takes the form of seed of cereals (for example wheat, barley, rye, millet and oats), corn, cotton, soya beans, rice, potatoes, sunflowers, coffee, tobacco, canola, oilseed rape, beets (for example sugarbeets and fodder beets), peanuts, vegetables (for example tomatoes, cucumbers, bean, cruciferous vegetables, onions and lettuce), fruit plants, lawns and ornamental plants. The treatment of the seed of cereals (such as wheat, barley, rye and oats), maize, soya beans, cotton, canola, oilseed rape and rice is of particular importance.

As already mentioned above, the treatment of transgenic seed with a compound of the formula (I) is also of particular importance. This takes the form of seed of plants which, as a rule, comprise at least one heterologous gene which governs the expression of a polypeptide with in particular insecticidal and/or nematicidal properties. The heterologous genes in transgenic seed can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. It is particularly preferably a heterologous gene derived from *Bacillus thuringiensis*.

In the context of the present invention, the compound of the formula (I) is applied to the seed. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water to a certain stage of the rice embryo ('pigeon breast stage'), stimulating the germination and a more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This must be ensured particularly in the case of active compounds which can exhibit phytotoxic effects at certain application rates.

In general, the compounds of the formula (I) are applied to the seed in a suitable formulation.

Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are prepared in a known manner, by mixing the compounds of the formula (I) with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of agrochemically active compounds. Preference is given to using alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are in particular lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Preference is given to using silicone antifoams and magnesium stearate.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions. Cellulose derivatives, acrylic acid derivatives, xanthan, modified clays and finely divided silica are preferred.

Adhesives which may be present in the seed dressing formulations usable in accordance with the invention are all customary binders usable in seed dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schidlingsbekampfungsmittel", vol. 2, Springer Verlag, 1970, pp. 401-412).

The seed dressing formulations usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or the use forms prepared therefrom by adding water, all mixing units usable customarily for the seed dressing are useful. Specifically, the procedure in the seed dressing is to place the seed into a mixer, operated batch-wise or continuously, to add the particular desired amount of seed dressing formulations, either as such or after prior dilution with water, and to mix everything until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. in the field of veterinary medicine, the compounds of the formula (I) are active against animal parasites, in particular ectoparasites or endoparasites. The term endoparasites includes in particular helminths and protozoans, such as coccidia. Ectoparasites are typically and preferably arthropods, in particular insects and acarids.

In the field of veterinary medicine the compounds of the formula (I) are suitable, with favourable homeotherm toxicity, for controlling parasites which occur in animal breeding and animal husbandry in livestock, breeding, zoo, laboratory, experimental and domestic animals. They are active against all or specific stages of development of the parasites.

Agricultural livestock include, for example, mammals, such as sheep, goats, horses, donkeys, camels, buffaloes, rabbits, reindeers, fallow deers, and in particular cattle and pigs; or poultry such as turkeys, ducks, geese, and in particular chickens; fish and crustaceans, for example in aquaculture; and also insects such as bees.

Domestic animals include, for example, mammals, such as hamsters, guinea pigs, rats, mice, chinchillas, ferrets and in particular dogs, cats, cage birds, reptiles, amphibians and aquarium fish.

According to a preferred embodiment, the compounds of the formula (I) are administered to mammals.

According to another preferred embodiment, the compounds of the formula (I) are administered to birds, namely cage birds and in particular poultry.

By using the compounds of the formula (I) to control animal parasites, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling" as used herein with regard to the animal health field, means that the compounds of the formula (I) are effective in reducing the incidence of the respective parasite in an animal infected with such parasites to innocuous levels. More specifically, "controlling", as used herein, means that the compound of the formula (I) is effective in killing the respective parasite, inhibiting its growth, or inhibiting its proliferation.

Arthropods include:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.; from the order of the Heteropterida, for example *Cimex* spp., *Triatoma* spp., *Rhodnius* spp., *Panstrongylus* spp.; as well as nuisance and hygiene pests from the order of the Blattarida.

Arthropods Furthermore Include:

from the subclass of the Acari (Acarina) and the order of the Metastigmata, for example from the family of argasidae like *Argas* spp., *Ornithodorus* spp., *Otobius* spp., from the family of Ixodidae like *Ixodes* spp., *Amblyomma* spp., *Rhipicephalus* (*Boophilus*) spp *Dermacentor* spp., *Haemophysalis* spp., *Hyalomma* spp., *Rhipicephalus* spp. (the original genus of multi-host ticks); from the order of mesostigmata like *Dermanyssus* spp., *Ornithonyssus* spp., *Pneumonyssus* spp., *Raillietia* spp., *Pneumonyssus* spp., *Stemostoma* spp., *Varroa* spp., *Acarapis* spp.; from the order of the Actinedida (*Prostigmata*), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic Protozoa include:

Mastigophora (*Flagellata*) such as, for example, Trypanosomatidae, for example, *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, such as, for example, Trichomonadidae, for example, *Giardia lamblia, G. canis;* Sarcomastigophora (*Rhizopoda*) such as Entamoebidae, for example, *Entamoeba histolytica*, Hartmanellidae, for example, *Acanthamoeba* sp., *Harmanella* sp.;

Apicomplexa (*Sporozoa*) such as Eimeridae, for example, *Eimeria acervulina, E. adenoides, E. alabamensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flave-* scens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium spec., Isospora belli, I. canis, I. felis, I. ohioensis, I. rivolta, I. spec., I. suis, Cystisospora spec., Cryptosporidium spec., in particular C. parvum; such as Toxoplasmadidae, for example, Toxoplasma gondii, Hammondia heydornii, Neospora caninum, Besnoitia besnoitii; such as Sarcocystidae, for example, Sarcocystis bovicanis, S. bovihominis, S. ovicanis, S. ovifelis, S. neurona, S. spec., S. suihominis, such as Leucozoidae, for example, Leucozytozoon simondi, such as Plasmodiidae, for example, Plasmodium berghei, P. falciparum, P. malariae, P. ovale, P. vivax, P. spec., such as Piroplasmea, for example, Babesia argentina, B. bovis, B. canis, B. spec., Theileria parva, Theileria spec., such as Adeleina, for example, Hepatozoon canis, H. spec.

Pathogenic endoparasites, which are helminths, include Platyhelmintha (e.g. Monogenea, cestodes and trematodes), nematodes, Acanthocephala, and Pentastoma, including:

Monogenea: e.g.: Gyrodactylus spp., Dactylogyrus spp., Polystoma spp.;

Cestodes: from the order of the Pseudophyllidea for example: Diphyllobothrium spp., Spirometra spp., Schistocephalus spp., Ligula spp., Bothridium spp., Diplogonoporus spp.;

from the order of the Cyclophyllida for example: Mesocestoides spp., Anoplocephala spp., Paranoplocephala spp., Moniezia spp., Thysanosoma spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.;

Trematodes: from the class of the Digenea for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fascioloides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp. Metorchis spp., Heterophyes spp., Metagonimus spp.;

Nematodes: Trichinellida zum Beispiel: Trichuris spp., Capillaria spp., Paracapillaria spp., Eucoleus spp., Trichomosoides spp., Trichinella spp.;

from the order of the Tylenchida for example: Micronema spp., Strongyloides spp.;

from the order of the Rhabditida for example: Strongylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Necator spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp. Parelaphostrongylus spp., Crenosoma spp., Paracrenosoma spp., Oslerus spp., Angiostrongylus spp., Aelurostrongylus spp., Filaroides spp., Parafilaroides spp., Trichostrongylus spp., Haemonchus spp., Ostertagia spp., Teladorsagia spp., Marshallagia spp., Cooperia spp., Nippostrongylus spp., Heligmosomoides spp., Nematodirus spp., Hyostrongylus spp., Obeliscoides spp., Amidostomum spp., Ollulanus spp.;

from the order of the Spirurida, for example: Oxyuris spp., Enterobius spp., Passalurus spp., Syphacia spp., Aspiculuris spp., Heterakis spp.; Ascaris spp., Toxascaris spp., Toxocara spp., Baylisascaris spp., Parascaris spp., Anisakis spp., Ascaridia spp.; Gnathostoma spp., Physaloptera spp., Thelazia spp., Gongylonema spp., Habronema spp., Parabronema spp., Draschia spp., Dracunculus spp.; Stephanofilaria spp., Parafilaria spp., Setaria spp., Loa spp., Dirofilaria spp., Litomosoides spp., Brugia spp., Wuchereria spp., Onchocerca spp., Spirocerca spp.;

Acanthocephala: from the order of the Oligacanthorhynchida, for example: Macracanthorhynchus spp., Prosthenorchis spp.; from the order of the Polymorphida, for example: Filicollis spp.; from the order of the Moniliformida, for example: Moniliformis spp.;

from the order of the Echinorhynchida, for example, Acanthocephalus spp., Echinorhynchus spp., Leptorhynchoides spp.;

Pentastoma: from the order of the Porocephalida, for example, Linguatula spp.

In the veterinary field and in animal keeping, administration of the compounds of the formula (I) is carried out by methods generally known in the art, such as enterally, parenterally, dermally or nasally in the form of suitable preparations. Administration can be carried out prophylactically or therapeutically.

Thus, one embodiment of the present invention refers to the use of a compound of the formula (I) as medicament.

A further aspect refers to the use of a compound of the formula (I) as an antiendoparasitic agent, in particular a helminthicidal agent or antiprotozoic agent. Compounds of the formula (1) are suitable for use as an antiendoparasitic agent, in particular a helminthicidal agent or antiprotozoic agent, for example in animal husbandry, in animal breeding, in animal housing and in the hygiene sector.

A further aspect in turn relates to the use of a compound of the formula (I) as an antiectoparasitic, in particular an arthropodicide such as an insecticide or an acaricide. A further aspect relates to the use of a compound of the formula (I) as an antiectoparasitic, in particular an arthropodicide such as an insecticide or an acaricide, for example in animal husbandry, in animal breeding, in stables or in the hygiene sector.

Vector Control

The compounds of the formula (I) can also be used in vector control. For the purpose of the present invention, a vector is an arthropod, in particular an insect or arachnid, capable of transmitting pathogens such as, for example, viruses, worms, single-cell organisms and bacteria from a reservoir (plant, animal, human, etc.) to a host. The pathogens can be transmitted either mechanically (for example trachoma by non-stinging flies) to a host, or by injection (for example malaria parasites by mosquitoes) into a host.

Examples of vectors and the diseases or pathogens they transmit are:
1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   *Simuliidae*: transmission of worms, in particular *Onchocerca volvulus*;
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia duttoni*, tick-borne encephalitis, Q fever (*Coxiella burnetii*), babesioses (*Babesia canis canis*).

Examples of vectors in the sense of the present invention are insects, for example aphids, flies, leafhoppers or *thrips*, which are capable of transmitting plant viruses to plants. Other vectors capable of transmitting plant viruses are spider mites, lice, beetles and nematodes.

Further examples of vectors in the sence of the present invention are insects and arachnids such as mosquitoes, in particular of the genera *Aedes, Anopheles*, for example *A. gambiae, A. arabiensis, A. funestus, A. dirus* (malaria) and *Culex*, lice, fleas, flies, mites and ticks capable of transmitting pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protecting wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. Likewise, the compounds of the formula (I), alone or in combinations with other active compounds, can be used as antifouling agents.

Control of Animal Pests in the Hygiene Sector

The compounds of the formula (I) are suitable for controlling animal pests in the hygiene sector. In particular, the invention can be applied in the domestic sector, in the hygiene sector and in the protection of stored products, especially for controlling insects, arachnids and mites encountered in enclosed spaces such as dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

They are used, for example, in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Reaction Schemes

The compounds of the invention may be made by the following methods.

The synthesis route for compounds of the invention (I-A) where R represents $(C_1-C_2)$-alkyl or $(C_1-C_2)$-halogenalkyl is shown below.

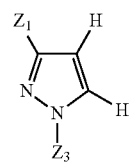  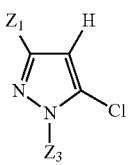 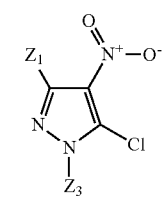

(1)　　　　　　(2)　　　　　　(3)

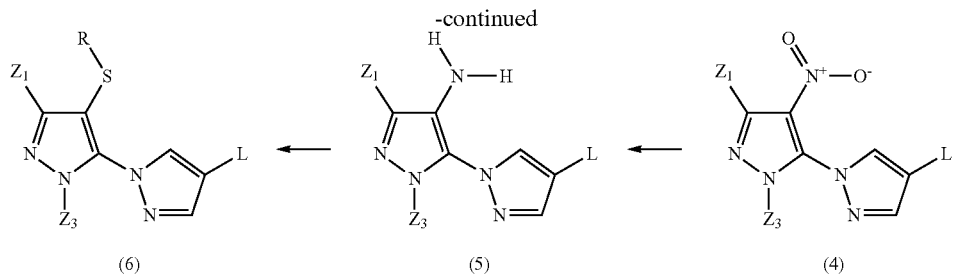

(6)  (5)  (4)

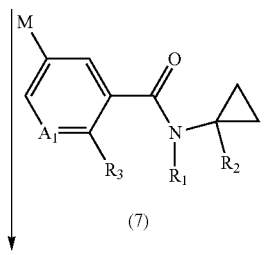

(7)

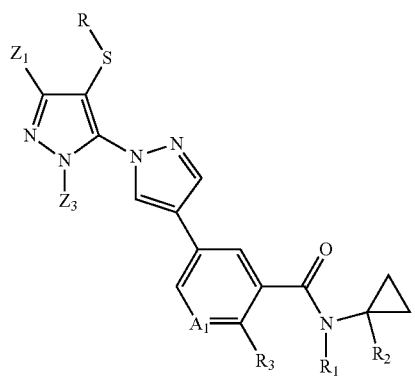

(I-A)

$Z_1$, $Z_3$, $R_1$, $R_2$, $R_3$ and $A_1$ represent the above described residues. L represents bromine or iodine, whereas M represents boronic acid, boronic acid esters or trifluoroboronate. R represents $(C_1-C_2)$-alkyl or $(C_1-C_2)$-halogenalkyl.

Compounds of formula (I-A) may be prepared by a transition metal (e.g. Palladium) catalysed reactions of a compound formula (6) with a compound of the formula (7). Those reactions may be performed in analogy to procedures described in literature [see, for example: WO2005-040110; WO2009-089508].

Compounds of the formula (7) are either commercially available or can be synthesized in analogy to procedures known from literature. Compounds of formula (6) may be synthesized in analogy to literature-known procedures from compounds of formula (5) [see, for example: WO2013-092522].

Compounds of formula (5) may be prepared by the reduction of compounds of formula (4). Suitable reducing agents may be Tin(II)chloride or Iron(0). Examples are widely described in literature [see, for example: Fe(0) WO2012-062783 or WO2014-023258; see, for example: Sn(II)Cl₂ WO2009-056556 or WO2002-016364].

Compounds of formula (4) may be prepared in a nucleophilic substitution from compounds of formula (3) and a corresponding pyrazole derivative. Examples for similar reactions are described in literature [see, for example: European Chemical Bulletin 2013, 2 (12), 981-984; Monatshefte fuer Chemie 1981, 112 (5), 675-678]. Compounds of formula (3) may be prepared starting from compounds of formula (2) by a nitration reaction. Similar reactions are described in literature [see, for example: EP1987-110490; DE1985-3528478]. Compounds of formula (2) may be prepared starting from compounds of formula (I) by a chlorination reaction. Similar reactions are described in literature [see, for example: WO2012-062783; WO2011-131615].

An example of a synthesis route for compounds of the invention (I-B) where R represents $(C_1-C_2)$-alkyl or $(C_1-C_2)$-halogenalkyl is shown below.

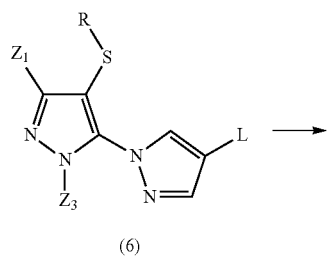

(6)

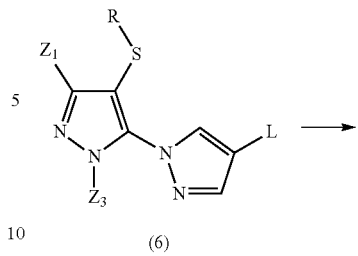

(6)

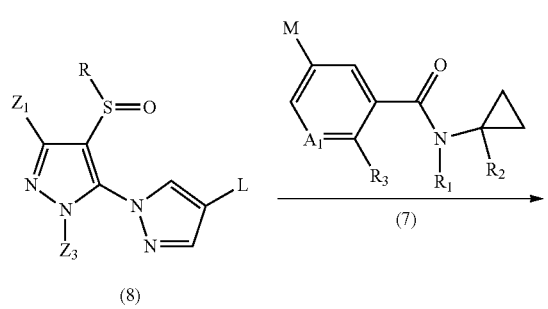

(8)

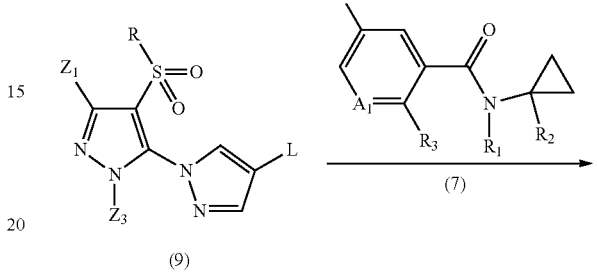

(9)

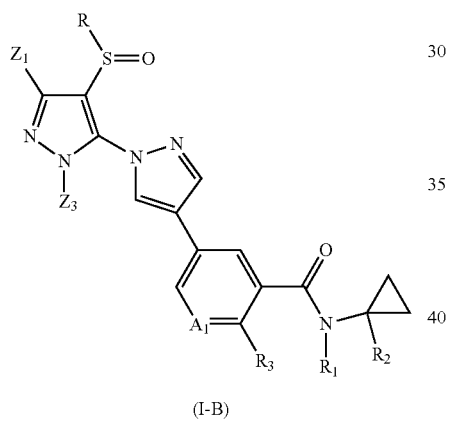

(I-B)

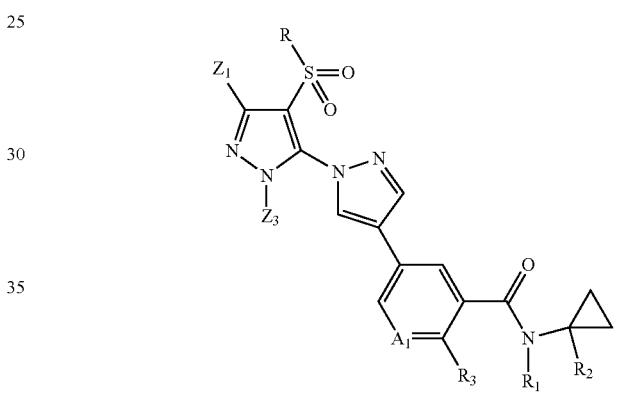

(I-C)

$Z_1$, $Z_3$, $R_1$, $R_2$, $R_3$ and $A_1$ represent the above described residues. L represents bromine or iodine, whereas M represents boronic acid, boronic acid esters or trifluoroboronate. R represents ($C_1$-$C_2$)-alkyl or ($C_1$-$C_2$)-halogenalkyl.

Compounds of formula (I-B) can be synthesized by reacting compounds of formula (7) and compounds of formula (8) in a transition metal catalysed reaction. The same reaction conditions as described for the synthesis of (I-A) from (6) and (7) can be applied. Compounds of formula (8) can be synthesized by an oxidation of compounds of formula (6). Suitable oxidants are e.g. m-chlorperbenzoic acid and hydrogen peroxide. Suitable procedures are already described in literature [see, for example: WO2010-035915; WO2007-138050]. The general synthesis of compounds of formula (6) has been already described above.

An example of a synthesis route for compounds of the invention (I-C) where R represents ($C_1$-$C_2$)-alkyl or ($C_1$-$C_2$)-halogenalkyl is shown below.

$Z_1$, $Z_3$, $R_1$, $R_2$, $R_3$ and $A_1$ represent the above described residues. L represents bromine or iodine, whereas M represents boronic acid, boronic acid esters or trifluoroboronate. R represents ($C_1$-$C_2$)-alkyl or ($C_1$-$C_2$)-halogenalkyl.

Compounds of formula (I-C) can be synthesized by reacting compounds of formula (7) and compounds of formula (9) in a transition metal catalysed reaction. The same reaction conditions as described for the synthesis of (I-A) from (6) and (7) can be applied. Compounds of formula (9) can be synthesized by an oxidation of compounds of formula (6). Suitable oxidants are e.g. m-chlorperbenzoic acid and hydrogen peroxide. Suitable procedures are already described in literature [see, for example: WO2013-018804; WO2007-138050]. The general synthesis of compounds of formula (6) has been already described above.

All starting materials employed can either be prepared by or analogously to processes known from the literature or are commercially available. Thus, for example, 1-methyl-3-(pentafluoroethyl)-1H-pyrazole can be prepared by a method known from the literature [e.g., WO2010-133312].

EXPERIMENTAL PART
Synthesis of 2-chloro-N-(1-cyanocyclopropyl)-5-[2'-methyl-4'-(methylsulfanyl)-5'-(pentafluoroethyl)-2'H-1,3'-bipyrazol-4-yl]benzamide (I-2)
5-chloro-1-methyl-3-(pentafluorethyl)-1H-pyrazole (11)
4.0 g (20 mmol) 1-methyl-3-(pentafluorethyl)-1H-pyrazole (10) were dissolved under argon atmosphere in 12 mL THF abs. and cooled to −75° C. The solution was treated
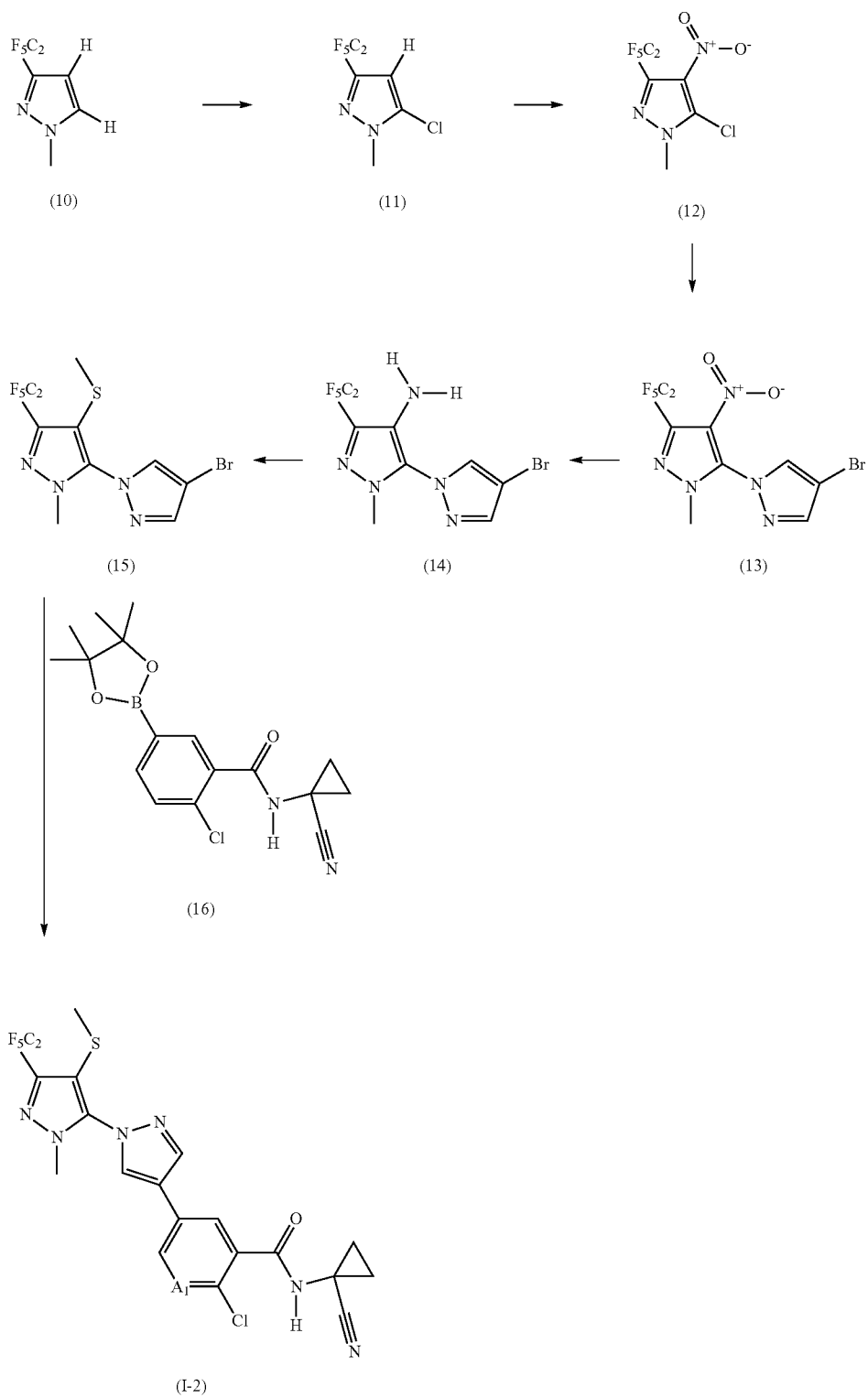

dropwise with 18.7 mL (30 mmol) n-butyllithium as 1.6 M solution in hexanes. The mixture was stirred for 45 minutes at −75° C. 5.68 g (24 mmol) hexchlorethane were dissolved in 20 mL THF abs. under argon atmosphere and cooled to −75° C. The pyrazole reaction mixture was transferred slowly via Teflon canula to the cooled hexachloroethane solution. The combined reaction mixture was stirred 1 h at −75° C. The reaction was quenched by the addition of saturated sodium bicarbonate solution. The reaction mixture was warmed to room temperature. The crude product was extracted several times with ethyl acetate. The combined organic phases were dried over $Na_2SO_4$, filtered and concentrated under vacuum (max. 35° C.; >80 mbar).

4.67 g 5-chloro-1-methyl-3-(pentafluorethyl)-1H-pyrazole (11) were isolated as colorless liquid. The crude product was used without further purification steps.

GC-MS**[)]: Index=908, Masse (m/z)=234 [M]$^+$.
$^1$H-NMR (400 MHz, acetonitrile-d3): 6.68 (s, 1H), 3.88 (s, 3H).

5-chloro-1-methyl-4-nitro-3-(pentafluoroethyl)-1H-pyrazole (12)

A mixture of 4.46 mL conc. fuming nitric acid and 12.12 mL conc. sulfuric acid was heated to 70° C. and then treated dropwise with 2.92 g (9.95 mmol) 5-chloro-1-methyl-3-(pentafluoroethyl)-1H-pyrazole (11) while keeping the temperature of the reaction below 90° C. The mixture was stirred 2 h at 75° C. The mixture was transferred into a water/ice mixture. The water phase was extracted several times with ethyl acetate. The combined organic phases were washed with 1N hydrochloric acid and brine. The organic phase was dried over $Na_2SO_4$, filtered and concentrated under vacuum. The crude product was taken up in toluene and concentrated under reduced pressure to remove traces of ethyl acetate and acetic acid.

2.24 g 5-chloro-1-methyl-4-nitro-3-(pentafluoroethyl)-1H-pyrazole (12) were isolated and used in the next step without purification.

GC-MS**[)]: Index=1280, Masse (m/z)=279 [M]+.
$^1$H-NMR (400 MHz, acetonitrile-d3): 3.93 (s, 3H).

4-bromo-2'-methyl-4'-nitro-5'-(pentafluoroethyl)-2'H-1,3'-bipyrazole (13)

1.74 g (6.23 mmol) 5-chloro-1-methyl-4-nitro-3-(pentafluoroethyl)-1H-pyrazole (12) and 1.04 g (6.86 mmol) 4-bromo-1H-pyrazole were dissolved in 26 mL THF abs. The mixture was treated with 1.72 g (12.4 mmol) potassium carbonate and heated to 50° C. for 4 h. The cooled reaction mixture was filtered and concentrated under vacuum. The crude product was purified using column chromatography.

0.25 g 4-bromo-2'-methyl-4'-nitro-5'-(pentafluoroethyl)-2'H-1,3'-bipyrazole (13) were isolated as colorless solid.
GC-MS**[)]: Index=1745, Masse (m/z)=389 [M]+.
$^1$H-NMR (400 MHz, acetonitrile-d3): 8.10 (s, 1H), 7.95 (s, 1H), 3.79 (s, 3H).

4-bromo-2'-methyl-5'-(pentafluoroethyl)-2'H-1,3'-bipyrazol-4'-amine (14)

701 mg (3.69 mmol) tin(II)chloride was dissolved in 2 mL Ethanol p.a. A solution of 365 mg (0.93 mmol) 4-bromo-2'-methyl-4'-nitro-5'-(pentafluoroethyl)-2'H-1,3'-bipyrazole (13) in 2 mL Ethanol p.a. was added and the reaction mixture was refluxed for 2 h. The reaction mixture was cooled with ice and then treated with conc. sodium hydroxide solution until the mixture reached pH9. The mixture was diluted with water and stirred for 20 minutes. The reaction mixture was extracted several times with dichloromethane. The combined organic phases were dried over $Na_2SO_4$, filtered and concentrated under vacuum.

267 mg 4-bromo-2'-methyl-5'-(pentafluoroethyl)-2'H-1,3'-bipyrazol-4'-amine (14) were isolated and used in the next step without further purification.

HPLC-MS*[)]: log P=2.68, Masse (m/z)=360 [M+H]$^+$.
$^1$H-NMR (400 MHz, DMSO-d6): 7.91 (s, 1H), 7.84 (s, 1H), 3.69 (broad s, 2H), 3.59 (s, 3H).

4-bromo-2'-methyl-4'-(methylsulfanyl)-5'-(pentafluoroethyl)-2'H-1,3'-bipyrazole (15)

2.0 g (5.55 mmol) 4-bromo-2'-methyl-5'-(pentafluoroethyl)-2'H-1,3'-bipyrazol-4'-amine (14) and 1.05 g (11.1 mmol) dimethyl disulfide were dissolved in 35 mL acetonitrile p.a. and treated with a solution of 1.10 mL t-butyl nitrite in 11 mL acetonitrile p.a. The reaction mixture was stirred for 1 h. The mixture was transferred into 1N hydrochloric acid. The water phase was extracted several times with ethyl acetate. The combined organic phases were washed with brine and dried over $Na_2SO_4$, filtered and concentrated under vacuum. The crude product was first purified via column chromatography and then purified via preparative HPLC.

740 mg 4-bromo-2'-methyl-4'-(methylsulfanyl)-5'-(pentafluoroethyl)-2'H-1,3'-bipyrazole (15) was isolated as colorless solid.

HPLC-MS*[)]: log P=3.95, Masse (m/z)=392 [M+H]$^+$.
$^1$H-NMR (400 MHz, DMSO-d6): 8.05 (s, 1H), 7.90 (s, 1H), 3.76 (s, 3H), 2.11 (s, 3H).

2-chloro-N-(1-cyanocyclopropyl)-5-[2'-methyl-4'-(methylsulfanyl)-5'-(pentafluoroethyl)-2'H-1,3'-bipyrazol-4-yl]benzamide (I-2)

740 mg (1.89 mmol) 4-bromo-2'-methyl-4'-(methylsulfanyl)-5'-(pentafluoroethyl)-2'H-1,3'-bipyrazole (15), 655 mg (1.89 mmol) 2-chloro-N-(1-cyanocyclopropyl)-5-(4,4,5,5-tetramethyl-1,3,2-dioxaborolan-2-yl)benzamide (16) and 109 mg (0.09 mmol) tetrakis(triphenylphosphine)palladium were dissolved in a freshly degassed mixture of 5.76 mL 1 M sodium bicarbonate solution and 53 mL 1,4 dioxane p.a. The mixture was heated under reflux for 3 h. The mixture was concentrated under vacuum. The residue was dissolved in water and ethyl acetate. The water phase was extracted with ethyl acetate. The organic phase was washed with water and dried over $Na_2SO_4$, filtered and concentrated under vacuum. The crude product was purified using column chromatography.

525 mg 2-chloro-N-(1-cyanocyclopropyl)-5-[2'-methyl-4'-(methylsulfanyl)-5'-(pentafluoroethyl)-2'H-1,3'-bipyrazol-4-yl]benzamide (I-2) was isolated as colorless solid.

HPLC-MS*[)]: log P=3.58, Masse (m/z)=531 [M+H]$^+$.
$^1$H-NMR (400 MHz, DMSO-d6): please refer to NMR peak list.

TABLE 1

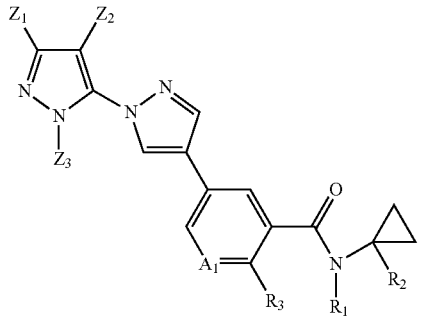

(I)

| Ex. No | $Z^1$ | $Z^2$ | $Z^3$ | $A_1$ | $R^1$ | $R_2$ | $R_3$ | logP[*] | Mass [m/z][*] | Angle of rotation |
|---|---|---|---|---|---|---|---|---|---|---|
| I-01 | $CF_3$ | SOMe | Me | CH | H | CN | Cl | 2.16 | 497 | |
| I-02 | $C_2F_5$ | SMe | Me | CH | H | CN | Cl | 3.56 | 531 | |
| I-03* | $C_2F_5$ | SOMe | Me | CH | H | CN | Cl | 2.61 | 547 | |
| I-04 | $C_2F_5$ | $SO_2Me$ | Me | CH | H | CN | Cl | 2.77 | 563 | |
| I-05 | $CF_3$ | $SO_2Me$ | Me | CH | H | H | Cl | 2.34 | 488 | |
| I-06 | $C_2F_5$ | SOMe | Me | CH | H | H | Cl | 2.60 | 522 | |
| I-07 | $C_2F_5$ | $SO_2Me$ | Me | CH | H | H | Cl | 2.78 | 538.0 | |
| I-08* | $C_2F_5$ | SOMe* | Me | CH | H | CN | Cl | 2.59 | 547.0 | −66.0° |
| I-09 | $C_2F_5$ | $SO_2Me$ | Me | CH | H | H | Me | 2.75 | 518.1 | |
| I-10 | $C_2F_5$ | SOMe | Me | N | H | CN | Me | 1.99 | 528.1 | |
| I-11 | $C_2F_5$ | SEt | Me | CH | H | H | Cl | 3.85 | 520.3 | |
| I-12 | $C_2F_5$ | SMe | Me | CH | H | H | Cl | 3.65 | 506.0 | |
| I-13 | $C_2F_5$ | SiPr | Me | CH | H | CN | Cl | 3.23 | 591.0 | |
| I-14 | $C_2F_5$ | SOMe | Me | N | H | H | Me | 1.85 | 503.0 | |
| I-15 | $C_2F_5$ | SEt | Me | CH | H | CN | Cl | 3.76 | 545.2 | |
| I-16 | $C_2F_5$ | SMe | Me | CH | H | CN | Me | 3.55 | 511.0 | |
| I-17 | $C_2F_5$ | SMe | Me | CH | H | H | Me | 3.64 | 486.1 | |
| I-18 | $C_2F_5$ | SOMe | Me | CH | H | H | Me | 2.57 | 502.0 | |
| I-19 | $C_2F_5$ | SMe | Me | N | Me | H | Cl | 3.67 | 521.0 | |
| I-20 | $C_2F_5$ | SOMe | Me | N | H | CN | Cl | 2.23 | 548.2 | |
| I-21* | $C_2F_5$ | SOMe* | Me | CH | H | CN | Cl | 2.59 | 547.0 | +65.1° |
| I-22 | $C_2F_5$ | SOEt | Me | CH | H | H | Cl | 2.88 | 536.1 | |
| I-23 | $C_2F_5$ | $SO_2Me$ | Me | CH | H | CN | Me | 2.79 | 543.0 | |
| I-24 | $C_2F_5$ | SOMe | Me | CH | H | CN | Me | 2.57 | 527.1 | 5 |
| I-25 | $C_2F_5$ | SOEt | Me | CH | H | CN | Cl | 2.84 | 560.9 | |

In the table, "Me" refers to methyl, "Et" refers to ethyl, "iPr" refers to iso-propyl

*I-08 and I-21 are enantiomers, I-03 is the racemic mixture thereof. The optical rotations were determined on a Perkin Elmer 341, serial number 9123, at a wavelength of 589 nm and a temperature of 20° C., by the following formula:

$$(\text{specific rotation } \alpha)_D^{*C} = \frac{\text{angle of rotation} * \text{volume of solution (ml)}}{\text{cell path length (dm)} * \text{initial mass (g)}}$$

The specific rotations in table I should be understood as an average from 5 different measurements ($CHCl_3$ (c = 0.009)).

The stated mass is the peak of the isotope pattern of the $[M + H]^+$ ion of the highest intensity; if the $[M - H]^-$ ion was detected, the stated mass is marked with [2].
[2]The stated mass is the peak of the isotope pattern of the $[M - H]^-$ ion of the highest intensity. If the mass was determined by a GCMS (see below for methods) measurement, the stated mass is marked with [3].
[3]Note regarding the determination of the logP values and mass detection:

The determination of the given logP values was carried out in accordance with EEC Directive 79/831 Annex V.A8 by HPLC (High Performance Liquid Chromatography) on a reversed-phase column (C18). Agilent 1100 LC system; 50*4.6 Zorbax Eclipse Plus C18 1.8 micron; mobile phase A: acetonitrile (0.1% formic acid); mobile phase B: water (0.09% formic acid); linear gradient from 10% acetonitrile to 95% acetonitrile in 4.25 min, then 95% acetonitrile for a further 1.25 min; oven temperature 55° C.; flow rate: 2.0 ml/min. Mass detection is carried out via an Agilend MSD system.

[**]Agilent 6890 GC, HP5979 MSD, 10 m DB-1, iD = 0.18 mm, FILM = 0.4 μm, Inj.: 250° C., const. flow: 1.6 mm/min He, Det.: MSD: 280° C., FID: 320° C., Oven: 50° C. (1 min) −40° C./min − 320° C. (3.25 min)

NMR Data of Selected Examples

NMR Peak List Method

1H-NMR data of selected examples are written in form of 1H-NMR-peak lists. To each signal peak are listed the δ-value in ppm and the signal intensity in round brackets. Between the δ-value-signal intensity pairs are semicolons as delimiters.

The peak list of an example has therefore the form:

$\delta_1$ (intensity$_1$); $\delta_2$ (intensity$_2$); ... ; $\delta_i$ (intensity$_i$); ... ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D$_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

Example I-1: $^1$H-NMR (400.0 MHz, CD3CN):
δ = 8.385 (4.4); 8.269 (4.1); 7.925 (0.9); 7.755 (0.5); 7.747 (2.4); 7.742 (2.8); 7.735 (0.4); 7.713 (1.7); 7.708 (1.2); 7.692 (1.6); 7.687 (1.3); 7.586 (1.2); 7.568 (0.6); 7547 (0.4); 7.522 (2.6); 7.501 (2.1); 6.870 (0.4); 5.447 (1.8); 4.050 (0.6); 4.050 (0.6); 3.830 (12.6); 3.772 (0.8); 2.888 (8.5); 2.767 (16.0); 2.670 (0.9); 2.137 (8.2); 2.114 (0.3); 2.108 (0.3); 1.972 (2.8); 1.964 (1.4); 1.957 (3.3); 1.952 (15.3); 1.946 (27.0); 1.940 (35.9); 1.934 (24.7); 1.927 (12.7); 1.600 (1.2); 1.586 (3.3); 1.579 (3.4); 1.565 (16); 1.437 (1.4); 1.363 (1.6); 1.350 (3.4); 1.343 (3.4); 1.328(1.2); 1.312 (0.3); 1.305 (0.4); 1.300 (0.4); 1.285 (0.7); 1.271 (0.8); 1.221 (0.7); 1.204(1.4); 1.186 (0.7); 0.146 (0.5); 0.008 (4.7); 0.000 (95.8); −0.008 (4.1); −0.149 (0.5)

Example I-2: $^1$H-NMR (400.0 MHz, CD3CN):
δ = 8.312 (5.7); 8.260 (5.4); 8.201 (0.3); 7.765 (3.1); 7.759 (4.1); 7.732 (2.2); 7.726 (1.6); 7.711 (2.4); 7.705 (2.2); 7.584 (0.6); 7.568 (1.5); 7.526 (3.8); 7.505 (3.1); 6.822 (0.3); 4.085 (0.5); 4.068 (1.4); 4.050 (1.4); 4.032 (0.5); 3.960 (1.1); 3.805 (16.0); 3.753 (0.4); 2.135 (117.2); 2.120 (1.8); 2.113 (1.9); 2.107 (2.2); 2.101 (1.5); 2.095 (0.8); 1.972 (6.8); 1.964 (9.3); 1.958 (22.9); 1.952 (133.4); 1.946 (243.9); 1.940 (330.1); 1.934 (228.3); 1.928 (118.5); 1.781 (0.8); 1.774 (1.4); 1.768 (1.5); 1.762 (1.4); 1.756 (0.7); 1.604 (1.7); 1.590 (4.3); 1.583 (4.3); 1.569 (2.2); 1.437 (1.6); 1.366 (2.2); 1.352 (4.1); 1.345 (4.4); 1.331 (1.7); 1.222 (1.7); 1.204 (3.3); 1.186 (1.6); 0.146 (2.1); 0.008 (14.0); 0.000 (456.7); −0.009 (17.3); −0.150 (2.0)

Example I-3: $^1$H-NMR (400.0 MHz, CD3CN):
δ = 8.409 (4.3); 8.281 (4.1); 8.079 (0.6); 8.072 (0.6); 7.904 (0.5); 7.899 (0.5); 7.755 (0.5); 7.750 (0.7); 7.742 (2.4); 7.736 (3.2); 7.712 (1.7); 7.706 (1.5); 7.691 (1.8); 7.685 (1.5); 7.632 (1.1); 7.570 (0.5); 7.549 (0.4); 7.522 (2.8); 7.501 (2.3); 6.619 (0.4); 6.614 (0.5); 6.608 (0.3); 5.448 (0.4); 4.086 (0.5); 4.068 (1.6); 4.050 (1.6); 4.032 (0.5); 3.820 (12.0); 3.765 (2.8); 2.707 (16.0); 2.600 (4.0); 2.156 (117.9); 2.114 (0.4); 2.108 (0.5); 2.102 (0.4); 1.972 (7.1); 1.965 (2.2); 1.959 (5.7); 1.953 (30.8); 1.947 (55.7); 1.940 (74.5); 1.934 (51.1); 1.928 (26.1); 1.775 (0.3); 1.769 (0.5); 1.763 (0.3); 1.598 (1.4); 1.584 (3.5); 1.577 (3.5); 1.563 (1.9); 1.437 (4.1); 1.363 (1.7); 1.349 (3.4); 1.342 (3.1); 1.328 (1.3); 1.276 (0.5); 1.270 (0.7); 1.222 (1.9); 1.204 (3.6); 1.186 (1.8); 0.008 (0.5); 0.000 (16.3); −0.008 (0.6)

Example I-4: $^1$H-NMR (400.0 MHz, CD3CN):
δ = 8.264 (10.6); 7.756 (2.4); 7.751 (3.0); 7.724 (1.5); 7.719 (1.1); 7.703 (1.8); 7.698 (1.4); 7.645 (0.4); 7.616 (1.5); 7.526 (2.8); 7.512 (0.4); 7.505 (2.3); 5.447 (2.5); 3.749 (12.6); 3.168 (16.0); 2.148 (126.0); 2.120 (0.6); 2.114 (0.6); 2.1607 (0.7); 2.101 (05); 1.972 (1.1); 1.964 (2.8); 1.958 (8.1); 1.952 (38.7); 1.946 (69.0); 1.940 (91.2); 1.934 (62.8); 1.928 (32.2); 1.775 (0.5); 1.769 (0.6); 1.762 (0.4); 1.600 (1.2); 1.585 (3.2); 1.578 (3.2); 1.565 (1.6); 1.363 (1.6); 1.350 (3.1); 1.343 (3.5); 1.328 (1.5); 1.270 (0.7); 1.204 (0.5); 0.000 (40.1)

Example I-5: $^1$H-NMR (600.1 MHz, d$_6$-DMSO):
δ = 8.809 (6.1); 8.560 (6.3); 8.554 (2.1); 8.546 (2.0); 7.775 (1.5); 7.771 (2.3); 7.759 (8.9); 7.551 (2.7); 7.549 (2.0); 7.538 (1.9); 7.536 (2.3); 3.833 (0.6); 3.820 (16.0); 3.333 (260.5); 3.319 (19.4); 3.243 (0.4); 2.859 (0.5); 2.852 (0.7); 2.846 (1.2); 2.839 (1.1); 2.834 (0.7); 2.827 (0.6); 2.523 (0.6); 2.520 (0.7); 2.616 (0.8); 2.508 (16.5); 2.505 (35.2); 2.502 (48.3); 2.499 (34.7); 2.496 (16.0); 1.989 (1.4); 1.186 (0.4); 1.175 (0.8); 1.163 (0.4); 0.725 (0.5); 0.717 (2.3); 0.714 (3.1); 0.705 (2.9); 0.702 (2.5); 0.694 (0.5); 0.557 (1.0); 0.550 (2.8); 0.546 (2.7); 0.543 (2.5); 0.540 (2.6); 0.531 (0.8)

Example I-6: $^1$H-NMR (400.0 MHz, CD3CN):
δ = 20.016 (0.5); 8.432 (4.6); 8.302 (4.3); 7.723 (2.8); 7.717 (3.5); 7.693 (2.0); 7.687 (1.5); 7.672 (2.0); 7.667 (1.6); 7.621 (0.4); 7.520 (3.2); 7.499 (2.3); 7.007 (1.0); 3.876 (1.9); 3.850 (12.8); 3.439 (0.4); 3.413 (0.4); 2.919 (1.1); 2.901 (0.9); 2.891 (1.2); 2.883 (1.4); 2.873 (1.4); 2.865 (0.9); 2.855 (0.7); 2.802 (0.9); 2.732 (16.0); 2.495 (2.8); 2.247 (140.1); 2.233 (214.8); 2.211 (1131.1); 2.150 (2.7); 2.144 (3.0); 2.138 (3.4); 2.132 (2.5); 1.993 (112.9); 1.988 (132.8); 1.983 (237.0); 1.976 (333.4); 1.970 (398.0); 1.964 (287.9); 1.958 (1.35.5); 1.811 (1.3); 1.805 (1.9); 1.799 (2.2); 1.793 (1.5); 1.787 (0.8); 1.299 (1.0); 0.825 (1.4); 0.807 (3.1); 0.795 (2.8); 0.778 (0.8); 0.642 (1.8); 0.631 (3.0); 0.624 (2.8); 0.602 (0.6); 0.110 (0.6); 0.029 (2.3)

Example I-07: $^1$H-NMR (400.0 MHz, CD3CN): δ = 8.268(0.4); 8.257(10.4); 7.709(2.2); 7.703(3.0); 7.677(1.5); 7.671(1.1); 7.656(1.7); 7.650(1.5); 7.494(2.8); 7.474(2.2); 7.003(0.7); 3.883(0.3); 3.748(11.9); 3.169(16.0); 2.874(0.5); 2.864(0.7); 2.856(1.1); 2.846(1.1); 2.837(0.7); 2.828(0.5); 2.479(0.7); 2.474(1.3); 2.469(1.8); 2.465(1.4); 2.460(0.7); 2.229(575.9); 2.135(0.3); 2.122(0.6); 2.116(1.0); 2.109(1.4); 2.103(1.0); 2.097(0.5); 1.966(6.1); 1.960(15.2); 1.954(87.2); 1.948(159.7); 1.942(216.0); 1.936(150.0); 1.930(77.9); 1.783(0.5); 1.777(0.9); 1.770(1.3); 1.764(0.9); 1.758(0.4); 0.797(0.6); 0.785(1.7); 0.780(2.3); 0.767(2.3); 0.762(1.7); 0.750(0.8); 0.614(0.7); 0.603(1.9); 0.597(2.0); 0.593(1.8); 0.588(1.8); 0.575(0.6); 0.008(1.0); 0.000(34.1); −0.008(1.3)

Example I-09: $^1$H-NMR (400.0 MHz, CD3CN): δ = 8.239(4.8); 8.230(4.9); 7.591(6.6); 7.573(2.2); 7.297(2.1); 7.277(1.8); 6.862(1.2); 3.748(14.5); 3.169(16.0); 3.122(0.5); 2.866(0.6); 2.856(0.9); 2.848(1.3); 2.838(1.3); 2.830(1.0); 2.820(0.7); 2.466(0.4); 2.379(13.8); 2.336(0.3); 2.181(315.6); 2.115(1.3); 2.109(1.3); 1.954(47.6); 1.948(82.3); 1.942(106.9); 1.937(81.6); 1.935(82.9); 1.770(0.7); 0.781(0.7); 0.764(3.2); 0.751(3.1); 0.735(1.1); 0.604(1.0); 0.592(3.1); 0.586(3.6); 0.566(0.9); 0.000(12.3)

Example I-10: $^1$H-NMR (400.0 MHz, CD3CN): δ = 8.829(2.8); 8.324(2.5); 8.432(4.7); 8.309(4.6); 8.038(0.5); 7.956(2.9); 7.951(2.7); 7.674(1.2); 7.587(0.5); 3.818(13.6); 3.061(0.6); 2.725(16.0); 2.586(14.3); 2.467(1.7); 2.463(2.1); 2.458(1.7); 2.412(0.6); 2.281(0.3); 2.249(0.4); 2.153(417.7); 2.119(2.8); 2.113(2.7); 2.106(2.8); 2.100(2.0); 2.094(1.1); 1.963(18.2); 1.951(172.9); 1.945(296.1); 1.939(376.7); 1.933(262.4); 1.927(135.8); 1.780(0.9); 1.774(1.7); 1.767(2.1); 1.761(1.5); 1.756(0.7); 1.590(1.1); 1.575(3.4); 1.569(3.5); 1.556(1.6); 1.363(1.6); 1.349(3.5); 1.343(3.3); 1.328(1.2); 1.270(0.4); −0.001(24.3)

Example I-11: $^1$H-NMR (400.0 MHz, CD3CN): δ = 8.305(5.6); 8.239(5.2); 7.705(3.1); 7.700(3.8); 7.673(2.0); 7.667(1.5); 7.652(2.2); 7.646(1.9); 7.490(3.4); 7.469(2.7); 7.421(1.0); 7.399(0.9); 7.394(0.9); 7.375(0.4); 7.361(0.5); 7.339(0.4); 6.908(1.1); 3.817(16.0); 3.777(0.7); 2.875(0.8); 2.865(0.9); 2.856(1.4); 2.847(1.5); 2.838(1.0); 2.829(0.8); 2.815(0.5); 2.535(1.5); 2.517(4.7); 2.499(4.9); 2.480(1.7); 2.139(219.0); 2.114(3.4); 2.108(3.0); 2.101(2.1); 2.047(0.3); 1.964(12.0); 1.952(126.1); 1.946(224.8); 1.940(297.7); 1.934(212.1); 1.928(115.4); 1.781(0.8); 1.775(1.3); 1.769(1.8); 1.763(1.4); 1.756(0.7); 1.368(0.4); 1.285(0.4); 1.269(0.6); 1.135(2.5); 0.994(5.0); 0.975(9.8); 0.957(4.8); 0.800(0.8); 0.782(3.3); 0.769(3.3); 0.764(3.1); 0.752(1.4); 0.745(1.0); 0.727(0.4); 0.615(1.0);0.604(3.1); 0.598(3.3); 0.589(2.9); 0.575(1.3); 0.567(1.0); 0.557(0.8); 0.146(3.4); 0.077(0.8); 0.000(686.5); −0.150(3.5)

Example I-12: $^1$H-NMR(400.0 MHz, CD3CN): δ = 8.300(5.5); 8.299(5.6); 8.260(0.4); 8.250(5.3); 8.248(5.1); 7.716(3.1); 7.710(4.0); 7.682(2.2); 7.676(1.7); 7.661(2.5); 7.655(2.2); 7.493(3.7); 7.472(3.0); 6.917(0.9); 3.803(16.0); 2.875(0.7); 2.866(1.0); 2.857(1.6); 2.848(1.6); 2.839(1.0); 2.830(0.7); 2.145(107.4); 2.135(24.8); 2.120(0.6); 2.114(0.8); 2.108(1.0); 2.102(0.7); 2.095(0.4); 1.972(1.0); 1.965(4.8);

-continued 1.959(11.7); 1.953(66.6); 1.947(121.7); 1.940(164.1); 1.934(112.2); 1.928(57.1); 1.915(0.6); 1.775(0.6); 1.769(0.9); 1.763(0.6); 1.135(1.9); 0.800(0.8); 0.788(2.4); 0.782(3.2); 0.770(3.3); 0.765(2.4); 0.752(1.1); 0.616(1.1); 0.604(2.7); 0.598(2.9); 0.594(2.5); 0.589(2.5); 0.577(0.8); 0.146(2.8); 0.033(0.4); 0.008(22.7); 0.000(609.2); −0.009(25.3); −0.150(2.7)

Example I-13: $^1$H-NMR(400.0 MHz, CD3CN): δ = 8.259(4.9); 8.245(4.6); 7.738(2.6); 7.732(3.4); 7.710(1.9); 7.705(1.3); 7.689(2.1); 7.684(1.7); 7.583(0.8); 7.570(1.5); 7.550(0.4); 7.520(3.2); 7.499(2.6); 4.068(0.6); 4.050(0.6); 3.821(0.3); 3.727(0.4); 3.711 (13.2); 3.382(0.4); 3.365(1.2); 3.348(1.6); 3.331(1.2); 3.314(0.5); 2.132(11.4); 2.113(2.2); 2.106(2.3); 2.100(1.6); 2.094(0.9); 1.971(3.5); 1.963(8.5); 1.957(22.3); 1.951(119.5); 1.945(217.9); 1.939(293.8); 1.933(206.6); 1.927(108.8); 1.780(0.7); 1.774(1.3); 1.767(1.8); 1.761(1.3); 1.755(0.7); 1.598(1.4); 1.584(3.5); 1.577(3.6); 1.564(1.9); 1.365(1.9); 1.351(3.5); 1.345(3.7); 1.330(1.4); 1.285(0.7); 1.270(1.2); 1.222(0.9); 1.205(16.0); 1.188(15.5); 0.146(1.4); 0.008(12.3); 0.000(330.8); −0.008(17.1); −0.150(1.5)

Example I-14: $^1$H-NMR(400.0 MHz, CD3CN): δ = 8.782(2.7); 8.777(2.6); 8.418(4.5); 8.295(4.2); 7.885(2.6); 7.880(2.5); 6.927(0.8); 5.446(0.8); 3.818(12.9); 3.070(1.6); 2.873(0.5); 2.864(0.8); 2.855(1.1); 2.846(1.2); 2.836(2.3); 2.828(0.6); 2.721(16.0); 2.564(13.9); 2.439(1.5); 2.130(122.5); 2.113(1.8); 2.106(1.5); 2.100(1.0); 2.094(0.6); 1.962(6.4); 1.951(70.6); 1.945(125.2); 1.939(166.6); 1.933(116.6); 1.927(60.4); 1.779(0.4); 1.773(0.7); 1.767(1.0); 1.761(0.7); 1.755(0.4); 1.271(0.4); 0.794(0.6); 0.781(1.9); 0.777(2.4); 0.764(2.4); 0.759(1.9); 0.747(0.8); 0.612(0.8); 0.601(2.4); 0.595(2.4); 0.586(2.0); 0.573(0.6); 0.146(3.7); 0.000(685.2); −0.008(40.4); −0.150(3.7)

Example I-15: $^1$H-NMR(400.0 MHz, CD3CN): δ = 8.319(5.8); 8.251(5.4); 7.754(3.2); 7.748(4.0); 7.723(2.1); 7.717(1.6); 7.702(2.5); 7.697(2.1); 7.606(0.9); 7.522(3.7); 7.501(3.0); 4.085(0.5); 4.068(1.5); 4.050(1.5); 4.032(0.5); 3.819(16.0); 2.629(0.3); 2.603(0.8); 2.537(1.6); 2.519(5.1); 2.500(5.2); 2.482(1.8); 2.155(63.6); 2.121(0.5); 2.114(0.6); 2.102(0.5); 1.972(6.9); 1.965(2.4); 1.959(5.7); 1.953(33.3); 1.947(61.5); 1.941(84.0); 1.935(58.8); 1.928(30.8); 1.775(0.4); 1.769(0.5); 1.763(0.4); 1.604(1.6); 1.589(4.1); 1.583(4.1); 1.569(2.1); 1.366(2.1); 1.352(4.2); 1.345(4.4); 1.331(1.6); 1.269(0.6); 1.222(1.8); 1.204(3.6); 1.186(1.8); 1.135(7.4); 0.994(5.3); 0.976(10.7); 0.958(5.1); 0.000(0.7)

Example I-16: $^1$H-NMR(400.0 MHz, CD3CN): δ = 8.267(5.4); 8.241(5.3); 7.649(7.0); 7.632(2.3); 7.466(1.6); 7.333(2.2); 7.313(1.9); 3.808(16.0); 2.403(15.5); 2.129(214.0); 2.106(2.1); 2.100(1.5); 2.094(0.9); 2.066(0.5); 2.055(0.6); 1.963(1827.9); 1.951(136.4); 1.945(190.5); 1.939(241.7); 1.933(168.8); 1.927(88.9); 1.791(12.5); 1.779(1.0); 1.774(1.3); 1.768(1.6); 1.761(1.1); 1.755(0.7); 1.581(1.5); 1.567(4.2); 1.560(4.2); 1.547(1.9); 1.357(1.9); 1.344(4.1); 1.337(4.1); 1.322(1.5); 1.271(0.4); 0.146(3.6); 0.045(0.4); 0.000(709.0); −0.150(3.6)

Example I-17: $^1$H-NMR(400.0 MHz, CD3CN): δ = 8.262(1.4); 8.251(6.0); 8.238(1.3); 8.227(5.7); 7.994(0.5); 7.931(0.4); 7.595(7.8); 7.578(2.5); 7.573(1.6); 7.296(2.5); 7.275(1.9); 6.805(1.3); 4.068(0.5); 4.050(0.5); 3.805(16.0); 3.711(0.6); 3.692(1.2); 2.877(0.5); 2.868(0.9); 2.859(1.3); 2.850(1.7); 2.841(1.5); 2.831(1.0); 2.823(0.7); 2.390(3.6); 2.380(15.9); 2.244(0.4); 2.144(93.1); 2.133(497.8); 2.113(2.7); 2.106(2.2); 2.100(1.6); 2.094(1.0); 2.071(0.4); 2.017(0.5); 1.962(30.4); 1.956(61.4); 1.951(135.2); 1.945(200.7); 1.939(246.6); 1.933(164.6); 1.927(81.9); 1.780(0.8); 1.774(1.2); 1.767(1.4); 1.761(0.9); 1.754(0.6); 1.222(0.6); 1.204(0.5); 1.186(0.7); 0.783(1.4); 0.770(3.0); 0.765(3.6); 0.753(3.5); 0.747(2.4); 0.736(1.2); 0.606(2.0); 0.596(3.8); 0.590(3.5); 0.580(2.0); 0.567(0.8); 0.157(1.1); 0.146(5.2); 0.078(0.6); 0.030(33.5); 0.011(187.2); 0.009(161.6); 0.000(1018.4); −0.008(49.0); −0.037(1.3); −0.070(0.4); −0.139(1.1); −0.150(5.3)

Example I-18: $^1$H-NMR(400.0 MHz, CD3CN): δ = 8.361(4.0); 8.254(3.8); 7.577(4.9); 7.572(2.1); 7.560(1.7); 7.556(1.0); 7.294(1.5); 7.273(1.3); 6.839(0.6); 3.841(0.4); 3.824(11.4); 3.801(0.4); 2.863(0.5); 2.854(0.7); 2.845(1.0); 2.836(1.0); 2.827(0.7); 2.817(0.5); 2.701(16.0); 2.376(11.1); 2.149(25.6); 2.108(0.4); 1.965(2.4); 1.958(3.8); 1.953(23.0); 1.947(42.0); 1.940(56.9); 1.934(39.4); 1.928(20.3); 1.769(0.3); 0.779(0.5); 0.767(1.7); 0.761(2.2); 0.749(2.3); 0.744(1.6); 0.732(0.8); 0.601(0.8); 0.590(2.0); 0.584(2.0); 0.580(1.8); 0.574(1.8); 0.562(0.5); 0.000(9.5); −0.009(0.4)

Example I-19: $^1$H-NMR(400.0 MHz, CD3CN): δ = 8.721(3.0); 8.715(3.1); 8.370(4.3); 8.369(4.5); 8.361(0.5); 8.290(4.1); 8.024(3.2); 8.018(3.2); 7.971(0.5); 7.964(0.5); 7.836(0.4); 6.832(0.4); 6.793(0.5); 5.447(5.4); 3.960(1.1); 3.877(1.6); 3.827(0.6); 3.808(13.5); 3.757(0.4); 3.072(16.0); 2.938(0.5); 2.886(0.4); 2.803(2.6); 2.788(0.6); 2.780(0.6); 2.772(1.2); 2.761(0.7); 2.753(0.6); 2.743(0.4); 2.158(101.8); 2.146(5.0); 2.120(0.4); 2.112(0.8); 2.107(0.6); 2.101(0.4); 1.964(2.7); 1.958(5.6); 1.952(30.6); 1.946(55.2); 1.940(73.8); 1.934(50.7); 1.927(26.0); 1.915(0.4); 1.768(0.4); 0.858(0.4); 0.838(0.3); 0.793(0.4); 0.781(0.4); 0.583(1.4); 0.537(1.9); 0.528(1.2); 0.520(1.7); 0.146(1.0); 0.008(8.2); 0.000(211.2); −0.009(8.5); −0.150(1.0)

Example I-20: $^1$H-NMR(400.0 MHz, CD3CN): δ = 8.749(2.8); 8.743(2.8); 8.469(4.3); 8.322(4.2); 8.118(3.1); 8.112(3.0); 7.704(0.6); 5.448(2.3); 3.815(12.3); 2.729(16.0); 2.158(11.7); 2.115(1.1); 2.108(1.0); 2.102(0.8); 2.096(0.6); 1.972(0.6); 1.965(1.6); 1.959(4.2); 1.953(22.0); 1.947(39.9); 1.941(53.4); 1.935(37.1); 1.928(19.4); 1.848(0.5); 1.769(0.3); 1.614(1.1); 1.599(3.0); 1.592(3.0); 1.579(1.5); 1.371(1.6); 1.357(3.0);1.351(3.0); 1.336(1.2); 0.008(0.5); 0.000(12.7)

Example I-22: $^1$H-NMR(400.0 MHz, CD3CN): δ = 8.395(5.6); 8.255(5.4); 7.694(0.5); 7.688(0.7); 7.678(3.3); 7.673(4.0); 7.649(2.2); 7.643(1.5); 7.628(2.3); 7.622(1.8); 7.527(0.4); 7.507(0.3); 7.485(3.5); 7.464(2.7); 6.951(1.2); 3.813(16.0); 3.280(1.2); 3.268(1.2); 3.026(0.5); 3.000(0.3); 2.981(1.0); 2.963(1.1); 2.949(1.5); 2.931(1.4); 2.912(0.5); 2.871(0.7); 2.861(1.1); 2.853(1.5); 2.843(1.5); 2.834(1.1); 2.825(0.7); 2.800(0.4); 2.781(1.3); 2.762(1.4); 2.748(1.1); 2.729(1.0); 2.711(0.3); 2.458(0.4); 2.157(134.1); 2.120(1.1); 2.113(0.8); 2.107(0.9); 2.101(0.6); 2.095(0.4); 1.952(45.7); 1.946(79.4); 1.940(103.1); 1.933(71.7); 1.927(37.4); 1.774(0.5); 1.768(0.6); 1.762(0.4); 1.271(0.8); 1.096(4.6); 1.077(9.3); 1.059(4.5); 0.795(0.8); 0.781(2.8); 0.777(3.5); 0.764(3.5); 0.759(2.8); 0.747(1.1); 0.612(1.2); 0.600(3.5); 0.595(3.5); 0.585(2.8); 0.573(0.8); 0.000(6.3)

Example I-23: $^1$H-NMR(400.0 MHz, CD3CN): δ = 8.280(4.1); 8.253(4.2); 8.202(0.5); 8.195(0.5); 7.674(5.5); 7.655(1.7); 7.567(1.2); 7.362(1.8); 7.343(1.5); 4.096(0.7); 4.079(0.7); 3.779(12.7); 3.199(16.0); 2.493(0.9); 2.450(0.6); 2.431(11.6); 2.189(381.6); 2.150(2.0); 2.143(2.1); 2.137(2.2); 2.131(1.7); 2.001(4.2); 1.994(7.1); 1.982(104.8); 1.976(191.7); 1.969(254.9); 1.963(182.7); 1.957(98.1); 1.862(0.4); 1.810(0.8); 1.804(1.3); 1.798(1.6); 1.792(1.2); 1.786(0.7); 1.607(1.2); 1.592(3.3); 1.586(3.5); 1.572(1.7); 1.466(2.5); 1.383(1.6); 1.369(3.7); 1.363(3.6); 1.348(1.7); 1.299(1.8); 1.250(1.0); 1.233(1.8); 1.215(0.6); 0.908(0.5); 0.887(0.6); 0.864(0.4); 0.029(0.4)

Example I-24: $^1$H-NMR(400.0 MHz, CD3CN: δ = 8.374(4.4); 8.269(4.3); 7.633(5.6); 7.616(1.9); 7.611(1.3); 7.582(0.8); 7.331(1.6); 7.310(1.4); 3.824(12.7); 2.705(16.0); 2.399(11.8); 2.195(87.9); 1.966(2.8); 1.954(13.9); 1.948(25.2); 1.942(33.9); 1.935(23.8); 1.929(12.4); 1.576(1.1); 1.562(3.1); 1.555(3.2); 1.542(1.5); 1.353(1.5); 1.340(3.1); 1.333(3.0); 1.319(1.1); 0.000(11.4)

Example I-25: $^1$H-NMR(400.0 MHz, CD3CN): δ = 8.434(5.7); 8.297(5.5); 8.099(0.5); 8.092(0.5); 7.919(0.4); 7.915(0.5); 7.760(3.1); 7.754(4.1); 7.731(2.2); 7.725(1.5); 7.710(2.5); 7.704(2.0); 7.614(1.2); 7.608(1.3); 7.549(4.0); 7.528(3.1); 6.900(0.6); 6.626(0.3); 6.621(0.4); 6.615(0.3); 4.097(0.9); 4.079(0.9); 4.062(0.3); 3.842(16.0); 3.789(2.6); 3.034(0.3); 3.015(1.1); 3.001(0.6); 2.997(1.2); 2.983(1.6); 2.978(0.5); 2.964(1.6); 2.946(0.5); 2.833(0.4); 2.814(1.4); 2.800(1.4); 2.795(1.4); 2.782(1.0); 2.777(0.5); 2.763(1.0); 2.744(0.5); 2.171(134.9); 2.150(1.0); 2.144(1.3); 2.137(1.6); 2.131(1.1); 2.125(0.6); 2.002(4.6); 1.994(6.4); 1.988(15.8); 1.982(97.4); 1.976(177.5); 1.970(240.1); 1.964(163.7); 1.958(83.9); 1.945(1.3); 1.811(0.6); 1.805(1.0); 1.798(1.4); 1.792(1.0); 1.786(0.5); 1.628(1.7); 1.614(4.0); 1.607(4.0); 1.594(2.4); 1.580(0.4); 1.573(0.4); 1.401(0.5); 1.392(2.2); 1.379(4.0); 1.372(4.1); 1.357(1.8); 1.353(1.4); 1.342(0.5); 1.335(0.5); 1.320(0.4); 1.315(0.6); 1.306(0.9); 1.299(0.9); 1.251(1.2); 1.233(2.3); 1.216(1.1); 1.164(2.0); 1.127(5.0); 1.109(10.4); 1.090(5.3); 1.070(1.9); 1.051(0.9); 0.029(0.7)

Biological Efficacy

*Ctenocephalides felis*—In-Vitro Contact Tests Adult Cat Flea 9 mg compound is solved in 1 ml acetone and diluted with acetone to the desired concentration. 250 μl of the test solution is filled in 25 ml glass test tubes and homogeneously distributed on the inner walls by rotation and tilting on a shaking device (2 h at 30 rpm). With a compound concentration of 900 ppm, an inner surface of 44.7 $cm^2$ and a homogeneous distribution, a dose of 5 $\mu g/cm^2$ is achieved.

After the solvent has evaporated, each test tube is filled with 5-10 adult cat fleas (*Ctenocephalides felis*), closed with a perforated lid and incubated in a lying position at room temperature and relative humidity. After 48 hours efficacy is determined. The fleas are patted on the ground of the tubes and are incubated on a heating plate at 45-50° C. for at most 5 minutes. Immotile or uncoordinated moving fleas, which are not able to escape the heat by climbing upwards, are marked as dead or moribund.

A compound shows good efficacy against *Ctenocephalides felis*, if at a compound concentration of 5 $\mu g/cm^2$ efficacy of at least 80% is monitored. An efficacy of 100% means all fleas are dead or moribund; 0% means no fleas are dead or moribund.

In this test, for example, the following compounds from the preparation examples showed good activity of 100% at an application rate of 5 $\mu g/cm^2$ (=500 g/ha): I-03, I-06, I-07, I-09, I-12, I-15, I-18

*Rhipicephalus sanguineus*—In-Vitro Contact Tests with Adult Brown Doe Ticks 9 mg compound is solved in 1 ml acetone and diluted with acetone to the desired concentration. 250 μl of the test solution is filled in 25 ml glass test tubes and homogeneously distributed on the inner walls by rotation and tilting on a shaking device (2 h at 30 rpm). With a compound concentration of 900 ppm, an inner surface of 44.7 $cm^2$ and a homogeneous distribution, a dose of 5 $\mu g/cm^2$ is achieved.

After the solvent has evaporated, each test tube is filled with 5-10 adult brown dog ticks (*Rhipicephalus sanguineus*), closed with a perforated lid and incubated in a lying position at room temperature and relative humidity. After 48 hours efficacy is determined. The ticks are patted on the ground of the tubes and are incubated on a heating plate at 45-50° C. for at most 5 minutes. Immotile or uncoordinated moving ticks, which are not able to escape the heat by climbing upwards, are marked as dead or moribund.

A compound shows a good efficacy against *Rhipicephalus sanguineus*, if at a compound concentration of 5 $\mu g/cm^2$ efficacy of at least 80% is monitored. An efficacy of 100% means all ticks are dead or moribund; 0% means no ticks are dead or moribund.

In this test, for example, the following compounds from the preparation examples showed good activity of 100% at an application rate of 5 $\mu g/cm^2$ (=500 g/ha): I-12, I-15

In this test, for example, the following compounds from the preparation examples showed good activity of 80% at an application rate of 5 $\mu g/cm^2$ (=500 g/ha): I-18

*Amblyomma hebraeum*—Test (AMBYHE)
Solvent: dimethyl sulfoxide

To produce a suitable preparation of active compound, 10 mg of active compound are dissolved in 0.5 ml solvent, and the concentrate is diluted with water to the desired concentration.

Tick nymphs (*Amblyomma hebraeum*) are placed in perforated plastic beakers and immersed in the aqueous compound solution for one minute. Ticks are transferred to a filter paper in a petridish and incubated in a climate chamber.

After 42 days mortality in % is determined. 100% means all the ticks have been killed; 0% means none of the ticks have been killed.

In this test, for example, the following compounds from the preparation examples showed good activity of 100% at an application rate of 100 ppm: I-02, I-07, I-11, 1-15

*Boophilus microplus*—Diptest (BOOPMI Dip)
Test animal: cattle ticks (*Boophilus microplus*) strane Parhurst, SP-resistant
Solvent: dimethyl sulfoxide To produce a suitable preparation of active compound, 10 mg of active compound are dissolved in 0.5 ml solvent, and the concentrate is diluted with water to the desired concentration.

This compound solution is pipetted into tubes. 8-10 engorged, adult, female cattle ticks (*Boophilus microplus*) are placed in perforated tubes. These tubes are immersed in the aqueous compound solution until the ticks are completely moistened. After the liquid has drained off, the ticks are transferred to a filter paper in a plastic tray and stored in a climate chamber.

After 7 days egg deposition of fertile eggs is monitored. Eggs where fertility is not visible are stored in a climate chamber till hatching after about 42 days. An efficacy of 100% means all eggs are infertile; 0% means all eggs are fertile.

In this test, for example, the following compounds from the preparation examples showed good activity of 100% at an application rate of 100 ppm: I-02, I-07, I-11, I-12, I-15

In this test, for example, the following compounds from the preparation examples showed good activity of 80% at an application rate of 100 ppm: I-09

*Boophilus microplus*—Injectiontest (BOOPMI Inj)
Solvent: dimethyl sulfoxide

To produce a suitable preparation of active compound, 10 mg of active compound are dissolved in 0.5 ml solvent, and the concentrate is diluted with solvent to the desired concentration.

Five adult engorged female ticks (*Boophilus microplus*) are injected with 1 μl compound solution into the abdomen. The ticks are transferred into replica plates and incubated in a climate chamber.

After 7 days egg deposition of fertile eggs is monitored. Eggs where fertility is not visible are stored in a climate chamber till hatching after about 42 days. An efficacy of 100% means all eggs are infertile; 0% means all eggs are fertile.

In this test, for example, the following compounds from the preparation examples showed good activity of 100% at an application rate of 20 μg/animal: I-02, I-03, I-04, I-05, I-06, I-07, I-09, I-11, I-12, I-15, I-18, I-20, I-23, I-24

*Ctenocephalides felis*—Oral Test (CTECFE)
Solvent: dimethyl sulfoxide

To produce a suitable preparation of active compound, 10 mg of active compound are dissolved in 0.5 ml solvent, and the concentrate is diluted with cattle blood to the desired concentration.

Approximately 20 adult unfed cat fleas (*Ctenocephalides felis*) are placed in flea chambers. The blood chamber, sealed with parafilm on the bottom, are filled with cattle blood supplied with compound solution and placed on the gauze covered top of the flea chamber, so that the fleas are able to suck the blood. The blood chamber is heated to 37° C. whereas the flea chamber is kept at room temperature.

After 2 days mortality in % is determined. 100% means all the fleas have been killed; 0% means none of the fleas have been killed.

In this test, for example, the following compounds from the preparation examples showed good activity of 100% at an application rate of 100 ppm: I-02, I-03, I-04, I-05, I-06, I-07, I-09, I-11, I-12, I-15, I-18, I-20, I-23, I-24

*Lucilia cuprina*—Test (LUCICU)
Solvent: dimethyl sulfoxide 10 mg active compound are dissolved in 0.5 ml Dimethylsulfoxid. Serial dilutions are made to obtain the desired rates.

Approximately 20 V1 instar larvae of the Australian sheep blowfly (*Lucilia cuprina*) are transferred into a test tube containing minced horse meat and compound solution of the desired concentration.

After 2 days mortality in % is determined. 100% means all the larvae have been killed; 0% means none of the larvae have been killed.

In this test, for example, the following compounds from the preparation examples showed good activity of 100% at an application rate of 100 ppm: I-02, I-03, I-04, I-06, I-07, I-11, I-12, I-15, I-18, I-20, I-23, I-24

In this test, for example, the following compounds from the preparation examples showed good activity of 90% at an application rate of 100 ppm: I-05, I-09

*Musca domestica*—Test (MUSCDO)
Solvent: dimethyl sulfoxide

To produce a suitable preparation of active compound, 10 mg of active compound are dissolved in 0.5 ml solvent, and the concentrate is diluted with water to the desired concentration.

10 adult house flies (*Musca domestica*) are transferred into a container, containing a sponge soaked with a mixture of sugar solution and compound solution of the desired concentration.

After 2 days mortality in % is determined. 100% means all the flies have been killed; 0% means none of the flies have been killed.

In this test, for example, the following compounds from the preparation examples showed good activity of 100% at an application rate of 100 ppm: I-03, I-04, I-06, I-07, I-11, I-12

In this test, for example, the following compounds from the preparation examples showed good activity of 90% at an application rate of 100 ppm: I-02, I-15, I-20

In this test, for example, the following compounds from the preparation examples showed good activity of 80% at an application rate of 100 ppm: I-09

*Myzus persicae*—Spray Test
Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Chinese cabbage (*Brassica pekinensis*) leaf disks infected with all instars of the green peach aphid (*Myzus persicae*), are sprayed with a preparation of the active ingredient of the desired concentration.

After 6 days mortality in % is determined. 100% means all aphids have been killed and 0% means none of the aphids have been killed.

In this test, for example, the following compounds from the preparation examples showed good activity of 100% at an application rate of 100 g/ha: I-01, I-02, I-04, I-09, I-10, I-11, I-13, I-16, I-18, I-19, I-20, I-22, I-24

In this test, for example, the following compounds from the preparation examples showed good activity of 90% at an application rate of 100 g/ha: I-03, I-06, I-07, I-12, I-14, I-15, I-17, I-25

In this test, for example, the following compounds from the preparation examples showed good activity of 100% at an application rate of 20 g/ha: I-23

*Phaedon cochleariae*—Spray Test
Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Chinese cabbage (*Brassica pekinensis*) leaf disks are sprayed with a preparation of the active ingredient of the desired concentration. Once dry, the leaf disks are infested with mustard beetle larvae (*Phaedon cochleariae*).

After 7 days mortality in % is determined. 100% means all beetle larvae have been killed and 0% means none of the beetle larvae have been killed.

In this test, for example, the following compounds from the preparation examples showed good activity of 100% at an application rate of 100 g/ha: I-01, I-02, I-03, I-04, I-05, I-06, I-07, I-11, I-12, I-13, I-14, I-15, I-16, I-17, I-18, I-19, I-20, I-22, I-23, I-24, I-25

*Spodoptera frugiperda*—Spray Test
Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Maize (*Zea mays*) leaf sections are sprayed with a preparation of the active ingredient of the desired concentration. Once dry, the leaf sections are infested with fall armyworm larvae (*Spodoptera frugiperda*).

After 7 days mortality in % is determined. 100% means all caterpillars have been killed and 0% means none of the caterpillars have been killed.

In this test, for example, the following compounds from the preparation examples showed good activity of 100% at an application rate of 100 g/ha: I-02, I-06, I-07, I-11, I-12, I-14, I-15

In this test, for example, the following compounds from the preparation examples showed good activity of 83% at an application rate of 100 g/ha: I-13, I-17, I-25

*Tetranychus urticae*—Spray Test OP-Resistant
Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

French bean (*Phaseolus vulgaris*) leaf disks which are heavily infested with all stages of the two spotted spidermite (*Tetranychus urticae*) are sprayed with a preparation of the active ingredient of the desired concentration.

After 6 days mortality in % is determined. 100% means all spider mites have been killed and 0% means none of the spider mites have been killed.

In this test, for example, the following compounds from the preparation examples showed good activity of 100% at an application rate of 100 g/ha: I-01, I-02, I-03, I-04, I-07, I-09, I-10, I-11, I-12, I-13, I-14, I-15, I-16, I-17, I-18, I-19, I-20, I-22, I-23, I-24, I-25

In this test, for example, the following compounds from the preparation examples showed good activity of 90% at an application rate of 100 g/ha: I-06

*Myzus persicae*—Spray Test
Solvent: 7 parts by weight of dimethylformamide
Emulsifier: alkylaryl polyglycol ether To produce a suitable preparation of active compound, 1 part by weight of active compound is mixed with the stated amount of solvent and is diluted with water, containing an emulsifier concentration of 1000 ppm, to the desired concentration. Further test concentrations are prepared by dilution with emulsifier containing water. Ammonium salt and/or penetration enhancer in a dosage of 1000 ppm are added to the desired concentration if necessary.

Pepper leaves (*Capsicum annuum*) which are heavily infested by the green peach aphid (*Myzus persicae*) are treated by being sprayed with the preparation of the active compound of the desired concentration.

After 6 days mortality in % is determined. 100% means all the aphids have been killed; 0% means none of the aphids have been killed.

In this test, for example, the following compounds from the preparation examples showed good activity of 100% at an application rate of 20 ppm: I-05

In this test, for example, the following compounds from the preparation examples showed good activity of 99% at an application rate of 20 ppm: I-06

In this test, for example, the following compounds from the preparation examples showed good activity of 98% at an application rate of 20 ppm: I-01

In this test, for example, the following compounds from the preparation examples showed good activity of 100% at an application rate of 4 ppm: I-03, I-04, I-08, I-12, I-13, I-22, I-24, I-25

In this test, for example, the following compounds from the preparation examples showed good activity of 99% at an application rate of 4 ppm: I-21

In this test, for example, the following compounds from the preparation examples showed good activity of 95% at an application rate of 4 ppm: I-20

In this test, for example, the following compounds from the preparation examples showed good activity of 80% at an application rate of 4 ppm: I-16

*Phaedon cochleariae*—Spray Test
Solvent: 7 parts by weight of dimethylformamide
Emulsifier: alkylaryl polyglycol ether To produce a suitable preparation of active compound, 1 part by weight of active compound is mixed with the stated amount of solvent and is diluted with water, containing an emulsifier concentration of 1000 ppm, to the desired concentration. Further test concentrations are prepared by dilution with emulsifier containing water. Ammonium salt and/or penetration enhancer in a dosage of 1000 ppm are added to the desired concentration if necessary.

Cabbage leaves (*Brassica oleracea*) are treated by being sprayed with the preparation of the active compound of the desired concentration and are infested with mustard beetle larvae (*Phaedon cochleariae*).

After 7 days mortality in % is determined. 100% means all the beetle larvae have been killed and 0% means none of the beetle larvae have been killed.

In this test, for example, the following compounds from the preparation examples showed good activity of 100% at an application rate of 4 ppm: I-02, I-03, I-04, I-07, I-08, I-12, I-13, I-15, I-16, I-21, I-25

*Tetranychus urticae*—Spray Test; OP-Resistant
Solvent: 7 parts by weight of dimethylformamide
Emulsifier: alkylaryl polyglycol ether To produce a suitable preparation of active compound, 1 part by weight of active compound is mixed with the stated amount of solvent and is diluted with water, containing an emulsifier concentration of 1000 ppm, to the desired concentration. Further test concentrations are prepared by dilution with emulsifier containing water. Ammonium salt and/or penetration enhancer in a dosage of 1000 ppm are added to the desired concentration if necessary.

Bean plants (*Phaseolus vulgaris*) which are heavily infested with all stages of the two-spotted spider mite (*Tetranychus urticae*) are treated by being sprayed with the preparation of the active compound of the desired concentration.

After 7 days mortality in % is determined. 100% means all the spider mites have been killed and 0% means none of the spider mites have been killed.

In this test, for example, the following compounds from the preparation examples showed good activity of 100% at an application rate of 20 ppm: I-01

In this test, for example, the following compounds from the preparation examples showed good activity of 90% at an application rate of 20 ppm: I-06

In this test, for example, the following compounds from the preparation examples showed good activity of 100% at an application rate of 4 ppm: I-02, I-03, I-04, I-07, I-08, I-12, I-13, I-15, I-16, I-20, I-23, I-24

In this test, for example, the following compounds from the preparation examples showed good activity of 95% at an application rate of 4 ppm: I-25

The invention claimed is:
1. A compound of formula (I),

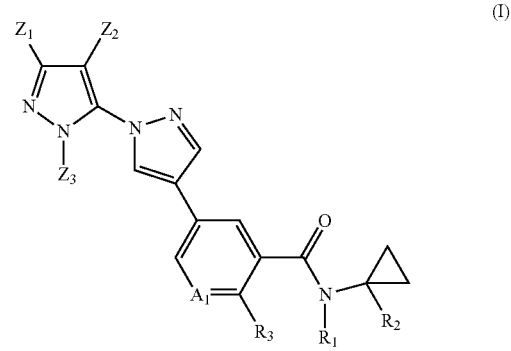

in which
$Z_1$ represents perhalogenated $(C_1-C_2)$-alkyl;
$Z_2$ represents $-S(O)_{0-2}-(C_1-C_2)$-alkyl or $-S(O)_{0-2}-(C_1-C_2)$-halogenalkyl;
$Z_3$ represents $(C_1-C_2)$-alkyl;

$R_1$ represents hydrogen (H) or ($C_1$-$C_2$)-alkyl;
$R_2$ represents H or cyano (CN);
$R_3$ represents $CH_3$ or chlorine (Cl); and
$A_1$ represents CH or nitrogen (N)
with the proviso that the two compounds characterized by the following combinations are excluded:

| $Z^1$ | $Z^2$ | $Z^3$ | $R^1$ | $A^1$ | $R^3$ | $R^2$ |
|---|---|---|---|---|---|---|
| —$CF_3$ | —S(O)—$CH_3$ | —$CH_3$ | —H | C—H | —Cl | —CN |
| —$CF_2CF_3$ | —S—$CH_3$ | —$CH_3$ | —H | C—H | —Cl | —CN. |

2. A compound according to claim 1, wherein $A_1$ is CH.
3. A compound according to claim 1, wherein $A_1$ is CH and $R_3$ is Cl.
4. A compound according to claim 1, wherein
$Z_1$ is $CF_3$ or $C_2F_5$;
$Z_2$ is —S—$CH_3$—S—$C_2H_5$, —S—$CF_3$, —S—$CH_2$—$CF_3$, —SO—$CH_3$, $SO_2$—$CH_3$, —SO—$C_2H_5$ or —$SO_2$—$C_2H_5$; and
$Z_3$ is $CH_3$.
5. A compound according to claim 1, wherein
$Z_1$ is $CF_3$ or $C_2F_5$;
$Z_2$ is —S—$CH_2CF_3$, —SO—$CH_2CF_3$, or $SO_2$—$CH_2CF_3$; and
$Z_3$ is $CH_3$.
6. A compound according to claim 1, wherein $R_1$ is H.
7. A compound according to claim 1, wherein $A_1$ is N.
8. A compound according to claim 1, wherein $R_3$ is Cl.
9. A method for controlling one or more insects, arachnids, and/or nematodes comprising applying a compound of formula (I) according to claim 1 to the one or more insects, arachnids and/or nematodes.
10. A pharmaceutical composition comprising at least one compound according to claim 1.
11. A medicament for the treatment of parasites in an animal comprising a compound according to claim 1.
12. A method for preparing a pharmaceutical composition for controlling parasites on one or more animals comprising combining a compound according to claim 1 with auxiliaries or further active compounds.
13. A compound selected from the group consisting of

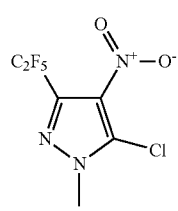

12

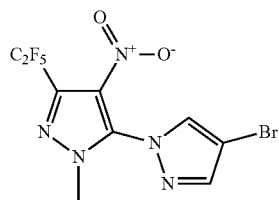

13

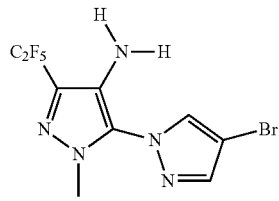

14

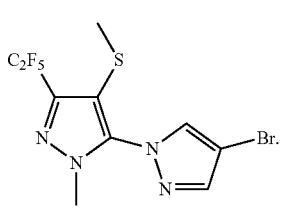

15

14. A method for controlling one or more pests, comprising applying a compound according to claim 1 to the pests and/or a habitat thereof.
15. A method for protecting a propagation material of one or more plants comprising applying a compound according to claim 1 to the propagation material of one or more plants or its habitat.
16. A method for protecting one or more plants and/or plant parts, comprising applying a compound according to claim 1 to the one or more plants and/or plant parts, their surroundings, habitat, or storage space.
17. A method for controlling parasites in livestock, breeding, zoo, laboratory, experimental, or domestic animal comprising administering a compound according to claim 1 to the animal.
18. A compound according to claim 1, wherein
$Z_1$ is $CF_3$ or $C_2F_5$;
$Z_2$ is —S—$CH_3$—S—$C_2H_5$, —SO—$CH_3$, $SO_2$—$CH_3$, or —SO—$C_2H_5$;
$Z_3$ is $CH_3$;
$A_1$ is CH or N;
$R_1$ is H;
$R_2$ is CN or H; and
$R_3$ is Cl or $CH_3$.

* * * * *